United States Patent
Kawamoto et al.

(10) Patent No.: US 12,391,921 B2
(45) Date of Patent: *Aug. 19, 2025

(54) METHOD FOR INDUCING ANTIGEN SPECIFIC CD8 POSITIVE T CELLS

(71) Applicant: KYOTO UNIVERSITY, Kyoto (JP)

(72) Inventors: Hiroshi Kawamoto, Kyoto (JP); Takuya Maeda, Kyoto (JP); Kyoko Masuda, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 574 days.

This patent is subject to a terminal disclaimer.

(21) Appl. No.: 17/724,907

(22) Filed: Apr. 20, 2022

(65) Prior Publication Data

US 2022/0251506 A1  Aug. 11, 2022

Related U.S. Application Data

(63) Continuation of application No. 16/092,411, filed as application No. PCT/JP2017/015358 on Apr. 14, 2017, now Pat. No. 11,401,504.

(30) Foreign Application Priority Data

Apr. 15, 2016 (JP) ................. 2016-082410

(51) Int. Cl.
| | |
|---|---|
| *C12N 5/0783* | (2010.01) |
| *A61K 40/11* | (2025.01) |
| *A61K 40/32* | (2025.01) |
| *A61K 40/42* | (2025.01) |
| *C12N 5/10* | (2006.01) |

(52) U.S. Cl.
CPC ............ *C12N 5/0636* (2013.01); *A61K 40/11* (2025.01); *A61K 40/32* (2025.01); *A61K 40/4243* (2025.01); *C12N 5/10* (2013.01); *A61K 2239/31* (2023.05); *A61K 2239/38* (2023.05); *A61K 2239/48* (2023.05); *C12N 2501/48* (2013.01); *C12N 2501/998* (2013.01); *C12N 2506/45* (2013.01)

(58) Field of Classification Search
CPC ................................... C12N 5/0636
See application file for complete search history.

(56) References Cited

U.S. PATENT DOCUMENTS

| | | |
|---|---|---|
| 2008/0213885 A1 | 9/2008 | Tryggvason et al. |
| 2009/0047263 A1 | 2/2009 | Yamanaka et al. |
| 2009/0068742 A1 | 3/2009 | Yamanaka et al. |
| 2010/0075241 A1 | 3/2010 | Caimi et al. |
| 2011/0117645 A1 | 5/2011 | Yasuda et al. |
| 2011/0287538 A1 | 11/2011 | Fusaki et al. |
| 2012/0220031 A1 | 8/2012 | Sekiguchi et al. |
| 2013/0078226 A1 | 3/2013 | Nakauchi et al. |
| 2017/0128556 A1 | 5/2017 | Kawamoto et al. |
| 2017/0296649 A1 | 10/2017 | Kawamoto et al. |
| 2017/0326175 A1 | 11/2017 | Kaneko et al. |
| 2017/0369850 A1 | 12/2017 | Kaneko et al. |

FOREIGN PATENT DOCUMENTS

| | | |
|---|---|---|
| EP | 2853590 A1 | 4/2015 |
| JP | 2014-514927 A | 6/2014 |
| WO | WO 2007069666 A1 | 6/2007 |
| WO | WO 2008118820 A2 | 10/2008 |
| WO | WO 2009007852 A2 | 1/2009 |
| WO | WO 2009032194 A1 | 3/2009 |
| WO | WO 2009057831 A1 | 5/2009 |
| WO | WO 2009058413 A1 | 5/2009 |
| WO | WO 2009079007 A1 | 6/2009 |
| WO | WO 20090775119 A1 | 6/2009 |
| WO | WO 2009091659 A2 | 7/2009 |
| WO | WO 2009101084 A1 | 8/2009 |
| WO | WO 2009101407 A2 | 8/2009 |
| WO | WO 2009102983 A2 | 8/2009 |
| WO | WO 2009114949 A1 | 9/2009 |
| WO | WO 2009117439 A2 | 9/2009 |
| WO | WO 2009123349 A1 | 10/2009 |
| WO | WO 2009126250 A2 | 10/2009 |
| WO | WO 2009126251 A2 | 10/2009 |
| WO | WO 2009126655 A2 | 10/2009 |
| WO | WO 2009157593 A1 | 12/2009 |

(Continued)

OTHER PUBLICATIONS

Osinska et al. (2014, Cenr. Eur. J Immunol., vol. 39(1), pp. 109-115.) (Year: 2014).*
Alberts et al., Molecular Biology of the Cell. 4th edition. New York: Garland Science; 2002. The Generation of Antibody Diversity. Available from: https://www.ncbi.nlrmnih.gov/books/N BK26860/ (Year: 2002).
Ando et al., "A safeguard system for induced pluripotent stem cell-derived rejuvenated T cell therapy," *Stem Dell Reports*, 5:597-608, 2015.
Arstila et al., A direct estimate of the human alphabeta T cell receptor diversity. Science. Oct. 29, 1999;286(5441):958-61. doi: 10.1126/science.286.5441.958. PMID:10542151.

(Continued)

*Primary Examiner* — Anoop K Singh
*Assistant Examiner* — David A Montanari
(74) *Attorney, Agent, or Firm* — LATHROP GPM LLP; James H. Velema, Esq.; Judith L. Stone-Hulslander, Esq.

(57) ABSTRACT

Provided is a method for inducing CD4⁻CD8⁺ T cells having an antigen specific cytotoxic activity from pluripotent stem cells, comprising the steps of: (1) differentiating pluripotent stem cells to give a cell culture comprising CD4⁻CD8⁻ T cells and CD4⁺CD8⁺ T cells, (2) removing CD4⁻CD8⁻ cells from the cell culture obtained in step (1), and (3) differentiating the CD4⁺CD8⁺ cells in the cell culture into CD4⁻CD8⁺ T cells.

19 Claims, 12 Drawing Sheets

Specification includes a Sequence Listing.

(56) References Cited

FOREIGN PATENT DOCUMENTS

| WO | WO 2010008054 A1 | 1/2010 |
|---|---|---|
| WO | WO 2010009015 A2 | 1/2010 |
| WO | WO 2010033906 A2 | 3/2010 |
| WO | WO 2010033920 A2 | 3/2010 |
| WO | WO 2010042800 A1 | 4/2010 |
| WO | WO 2010050626 A1 | 5/2010 |
| WO | WO 2010056831 A2 | 5/2010 |
| WO | WO 2010068955 A2 | 6/2010 |
| WO | WO 2010098419 A1 | 9/2010 |
| WO | WO 2010102267 A2 | 9/2010 |
| WO | WO 2010111409 A2 | 9/2010 |
| WO | WO 2010111422 A2 | 9/2010 |
| WO | WO 2010115050 A2 | 10/2010 |
| WO | WO 2010124290 A2 | 10/2010 |
| WO | WO 2010137746 A1 | 12/2010 |
| WO | WO 2010147395 A2 | 12/2010 |
| WO | WO 2010147612 A1 | 12/2010 |
| WO | WO 2011043405 A1 | 4/2011 |
| WO | WO 2011096482 A1 | 8/2011 |
| WO | WO 2013176197 A1 | 11/2013 |
| WO | WO 2015099134 A1 | 7/2015 |
| WO | WO 2016/010154 A1 | 1/2016 |
| WO | WO 201610153 A1 | 1/2016 |
| WO | WO 2016010148 A1 | 1/2016 |
| WO | WO 2016076415 A1 | 5/2016 |

OTHER PUBLICATIONS

Chen et al., "The role and mechanisms of double negative regulatory T cells in the suppression of immune responses", Cell Mol Immunol., 1(5):328-35, 2004.

Cheroutre et al. "Doubting the TCR coreceptor function of CD8alphaalpha", Immunity, (2):149-59, 2008.

Cyranoski et al., "Stem-cell pioneer banks on future therapies", Nature, 88:139, 2012.

Eminli et al., "Reprogramming of neural progenitor cells into induced pluripotent stem cells in the absence of exogenous Sox2," Stem Cells, 26:2467-2474, 2008.

Feng et al., "Reprogramming of fibroblasts into induced pluripotent stem cells with orphan nuclear receptor Esrrb", Nat. Cell Biol., 11:197-203, 2009.

Grskovic et al., "Induced pluripotent stem cells-opportunities for disease modelling and drug discovery," Nature Reviews Drug Discovery, 10:915-929, 2011.

Han et al., "Tbx3 improves the gem-line competency of induced pluripotent stem cells", Nature, 463:1096-1100, 2010.

Heng et al., "The nuclear receptor Nr5a2 can replace Oct4 in the reprogramming of murine somatic cells to pluripotent cells", Cell Stem Cell, 6:167-74, 2010.

Huangfu et al., "Induction of pluripotent stem cells from primary human fibroblasts with only Oct4 and Sox2", Nat. Biotechnol., 26:1269-1275, 2008.

Huangfu et al., "Induction of pluripotent stem cells by defined factors is greatly improved by small-molecule compounds", Nat. Biotechnol., 26:795-797, 2008.

Ichida et al., "A small-molecule inhibitor of Tgf-beta signaling replaces Sox2 in reprogramming by inducing Nanog", Cell Stem Cell, 5:491-503, 2009.

International Search Report for International Application No. PCT/JP2017/015358, mailing date Jul. 11, 2017, 2 pages. English translation.

International Preliminary Report on Patentability for International Patent Application No. PCT/JP2017/015358, dated Jan. 29, 2018.

Judson et al., "Embryonic stem cell-specific microRNAs promote induced pluripotency", Nat. Biotechnol., H:459-461, 2009.

Kaneko S., "In vitro generation of rejuvenated antigen-specific T cells by reprogramming to pluripotency and redifferentiation", Cell Stem Cell., 12:114-126, 2013.

Kawamoto H. et al., "Cloning and expansion of antigen-specific T cells using iPSC technology: A novel strategy for cancer immunotherapy", Inflammation and Regeneration, 35(5):220-225, 2015.

Kim et al., "Direct reprogramming of human neural stem cells by OCT4", Nature, 461:649-653, 2009.

Kitayama et al., "Cellular adjuvant properties, direct cytotoxicity of re-differentiated V-alpha24 invariant NKT-ells from human induced pluripotent stem cells", Stem Cell Reports, 6:213-227, 2016.

Lyssiotis et al., "Reprogramming of murine fibroblasts to induced pluripotent stem cells with chemical ,implementation of Klf4", Proc. Nat. Acad. Sci. USA, 106:8912-8917, 2009.

Maeda et al., "Regeneration of CD8αβ T cells from T-cell-derived iPSC imparts potent tumor antigen-specific cytoxicity", Cancer Research, 76(23):6839-6850, 2016.

Maekawa et al., "Direct reprogramming of somatic cells is promoted by maternal transcription factor Glis1", Nature, 474:225-9, 2011.

Mali et al., "Butyrate greatly enhances derivation of human induced pluripotent stem cells by promoting epigenetic remodeling and the expression of pluripotency-associated genes", Stem Cells, 28:713-720, 2010.

Marson et al., "Wnt Signalling Promotes Reprogramming of Somatic Cells to Pluripotency", Cell Stem Cell, 3:132-135, 2008.

Nakagawa et al., "Generation of induced pluripotent stem cells without Myc from mouse and human Fibroblasts", Nat. Biotechnol., 26:101-106, 2008.

Nakao et al., "Expansion of functional human mucosal-associated invariant T cells via reprogramming to pluripotency and redifferentiation", Cell Stem Cell, 12:546-558, 2013.

Narren et al., "Highly efficient reprogramming to pluripotency and directed differentiation of human cells with synthetic modified mRNA", Cell Stem Cell, 7:618-630, 2010.

Neko S., "In vitro generation of antigen-specific T cells from induced pluripotent stem cells of antigen-specific T cell origin", Methods in Molecular Biology, 1393:67-73, 2016.

Newell et al., "Beyond model antigens: high-dimensional methods for the analysis of antigen-specific T cells", Nat Biotechnol., 2014;32(2):149-157. doi:10.1038/nbt.2783 (Year: 2014).

Nishimura et al., "Development of detective and persistent sendai virus vector," J. Biol. Chem., 286:4760-4771, 2011.

Nishimura et al., "Generation of Rejuvenated Antigen-Specific T Cells by Reprogramming to Pluripotency and Redifferentiation", Cell Stem Cell, 12:114-126, 2013.

Saito et al., "Reprogramming of Melanoma Tumor-Infiltrating Lymphocytes to Induced Pluripotent Stem Cells", Stem Cells International, vol. 2016, Jan. 1, 2016, pp. 1-11.

Saito et al., "Adoptive Transfer of CD8+ T Cells Generated from Induced Pluripotent Stem Cells Triggers Regressions of Large Tumors Along with Immunological Memory", Cancer Research, 76(12):3473-3483, Apr. 12, 2016.

Schmitt et al. "New Strategies in Engineering T-cell Receptor Gene-Modified T cells to More Effectively Target Malignancies", Clin Cancer Res., 21(23):5191-5197, 2015.

Shi et al., "A combined chemical and genetic approach for the generation of induced pluripotent stem cells", Cell Stem Cell, 2:525-528, 2008.

Shi et al., "Induction of pluripotent stem cells from mouse embryonic fibroblasts by Oct4 and Klf4 with small-molecule compounds", Cell Stem Cell, 3:568-574, 2008.

Stadtfeld et al., "Induced pluripotent stem cells generated without viral integration", Science, 322:945-949, 2008.

Su et al., "Memory T Cell From Granzyme B Attack by Double-Negative T Regulatory Cell", American Journal of Transplantation, 14:580-593, 2014.

Sun et al., "Feeder-free derivation of induced pluripotent stem cells from adult human adipose stem cells", Proc. Natl. Acad. Sci. USA, 106:15720-15725, 2009.

Supplementary European Search Report in related European Application No. 17782533.8, dated Nov. 19, 2020 8 pages.

Takahashi et al., "Induction of pluripotent stem cells from mouse embryonic and ault fibroblasts cultures by lamed factors", Cell, 126:663-676, 2006.

(56) References Cited

OTHER PUBLICATIONS

Takahashi et al., "Induction of Pluripotent Stem Cells from Adult Human Fibroblasts by Defined Factors," *Cell*, 131:861-872, 2007.
Takahashi et al., "Human induced pluripotent stem cells on autologous feeders," PLoS One, 4:e8067, 2009.
Takuya M. et al., iPS Saibo Gijutsu o Mochiita WT1 Tokuiteki Killer T-saibo (CTL) no Saisei, Regenerative Medicine, vol. 15, Suppl., p. 258, 2016.
Themeli et al., "Generation of tumor-targeted human T lymphocytes from induced pluripotent stem cells for cancer therapy", *Nat. Biotechnol.*, 31(10):928-933, 2013.
Themeli et al., "New cell sources for T cell engineering and adoptive immunotherapy," *Cell Stem Cell*, 16:357-366, 2015.
Timmermans et al., "Generation of T Cells from Human Embryonic Stem Cell-Derived Hematopoietic Zones", *Journal of Immunology*, 182:6879-6888, 2009.
Tsuboi et al., "Enhanced induction of human WT1-specific cytotoxic T lymphocytes with a 9-mer WT1 peptide modified at HLA-A*2402-binding residues," *Cancer Immunol. Immunother.*, 51:614-620, 2002.
Yu et al., "Induced Pluripotent Stem Cell Lines Derived from Human Somatic Cells", *Science*, 318:1917-1920, 2007.
Vizcardo et al., "Regeneration of human tumor antigen-specific T cells from iPSCs derived from mature CD8+ T Cells", *Cell Stem Cell*, 12.31-36, 2013.
Zhao et al., "Two Supporting Factors Greatly Improve the Efficiency of Human iPSC Generation," *Cell Stem Cell*, 3:475-479, 2008.
Cyranoski et al., "Stem-cell pioneer banks on future therapies", Nature, Aug. 9, 2012, 488: 139.
Kaneko, "In Vitro Generation of Antigen-Specific T Cells from Induced Pluripotent Stem Cells of Antigen-Specific T Cell Origin", Tumor Immunology Methods and Protocols, Chapter 6, Apr. 1, 2016, Part of the Methods in Molecular Biology book series, 1393: 67-73, 2016.
Wakao et al., "Expansion of functional human mucosal-associated invariant T cells via reprogramming to pluripotency and redifferentiation", Cell Stem Cell, May 2, 2013, 12: 546-558.
Warren et al., "Highly efficient reprogramming to pluripotency and directed differentiation of human cells with synthetic modified mRNA", Cell Stem Cell, Nov. 5, 2010, 7: 618-630.

* cited by examiner

METHOD FOR INDUCING ANTIGEN SPECIFIC CD8 POSITIVE T CELLS

CROSS-REFERENCE TO RELATED APPLICATIONS

This application is a continuation of U.S. patent application Ser. No. 16/092,411, filed Oct. 9, 2018, which is a 35 U.S.C. § 371 filing of International Patent Application No. PCT/JP2017/015358, filed Apr. 14, 2017, which claims priority to Japanese Patent Application No. 2016-082410, filed Apr. 15, 2016, the entire contents of which are incorporated herein by reference.

ART RELATED

The present application relates to a method for inducing $CD4^-CD8^+$ T cells from pluripotent stem cells.

BACKGROUND ART

Each T cell expresses a T cell receptor (TCR) with different specificity. When an infectious disease develops, a T cell having a suitable specificity will proliferate to give a T cell population (clone) that will fight with the pathogen. This is the basic idea of the acquired immunity. If it is possible to artificially amplify a T cell with a desired specificity, the amplified T cells may be used for the adoptive immunotherapy. The amplification of a given T cell is referred to as "cloning". In fact, autologous transplantation of antigen specific T cells prepared by amplifying the antigen specific T cell obtained from the patient has been clinically conducted. However, almost all autologous T cell transplantation therapies do not use a cell population purified to the extent of "cloned" cells. In addition, repeated in vitro sub-culturing of the cells might cause loss of the function to kill the cancer cells.

A method for providing T cells that are capable of infinitely proliferate by immortalizing the cells has been proposed. A cell may be immortalized and proliferated to give a cloned cell population. Procedures to immortalize a cell may include fusion of the cell with a cancer cell as well as long term culture of the cells with stimulating TCR under the presence of cytokines. However, auto-transplantation of thus obtained immortalized T cells may be dangerous because the cells are so to speak cancer cells. In addition, the cloning procedures could lower the cell functions.

A method for generating pluripotent stem cells, especially iPS cells, bearing genes encoding a TCR specific for a given antigen, and a method for re-generating T cells bearing the TCR from the iPS cells have been reported (See Patent Literatures 1-7 and Non-Patent Literatures 1-6). Based on those methods, a large amount of T cells bearing genes encoding a specific TCR can be prepared. Those T cells are expected to be applied for cell-based immunotherapies.

For example, iPS cells can be induced from cytotoxic T lymphocytes and then, cytotoxic T lymphocytes can be re-generated from the iPS cells. Up to now, however, there is no report that the re-generated CTLs having cytotoxic activities comparative to the original CTLs from which the iPS cells were induced could be obtained.

CTLs generated in the living body are $CD4^-CD8^+$ T cells and the CD8 molecule is a $CD8\alpha\beta$ heterodimer. $CD8\alpha\alpha$ T cells are T cells of "innate immune type", and do not have sufficient binding affinity to MHC class I molecules and have weak function as a co-receptor of T cell receptor (TCR). $CD8\alpha\alpha$ type T cells are rarely contained in lymphoid tissues, and they are commonly found in mucosal tissues.

PRIOR ART DOCUMENTS

Patent Documents

[Patent Literature 1] WO2011/096482
[Patent Literature 2] WO2013/176197
[Patent Literature 3] WO2015/099134
[Patent Literature 4] WO2016/010148
[Patent Literature 5] WO2016/010153
[Patent Literature 6] WO2011/096482
[Patent Literature 7] WO2011/096482

Non Patent Document

[Non-Patent Literature 1] Vizcardo, R., Masuda, K., Yamada, D., Ikawa, T., Shimizu, K., Fujii, S., Koseki, H., and Kawamoto, H. (2013). Regeneration of human tumor antigen-specific T cells from iPSCs derived from mature CD8(+) T cells. Cell Stem Cell 12, 31-36.

[Non-Patent Literature 2] Nishimura, T., Kaneko, S., Kawana-Tachikawa, A., Tajima, Y., Goto, H., Zhu, D., Nakayama-Hosoya, K., Iriguchi, S., Uemura, Y., Shimizu, T., et al. (2013). Generation of rejuvenated antigen-specific T cells by reprogramming to pluripotency and redifferentiation. Cell Stem Cell 12, 114-126.

[Non-Patent Literature 3] Wakao, H., Yoshikiyo, K., Koshimizu, U., Furukawa, T., Enomoto, K., Matsunaga, T., Tanaka, T., Yasutomi, Y., Yamada, T., Minakami, H., et al. (2013). Expansion of functional human mucosal-associated invariant T cells via reprogramming to pluripotency and redifferentiation. Cell Stem Cell 12, 546-558.

[Non-Patent Literature 4] Themeli, M., Kloss, C. C., Ciriello, G., Fedorov, V. D., Perna, F., Gonen, M., and Sadelain, M. (2013). Generation of tumor-targeted human T lymphocytes from induced pluripotent stem cells for cancer therapy. Nat Biotechnol 31, 928-933.

[Non-Patent Literature 5] Ando, M., Nishimura, T., Yamazaki, S., Yamaguchi, T., Kawana-Tachikawa, A., Hayama, T., Nakauchi, Y., Ando, J., Ota, Y., Takahashi, S., et al. (2015). A Safeguard System for Induced Pluripotent Stem Cell-Derived Rejuvenated T Cell Therapy. Stem Cell Reports 5, 597-608.

[Non-Patent Literature 6] Kitayama, S., Zhang, R., Liu, T. Y., Ueda, N., Iriguchi, S., Yasui, Y., Kawai, Y., Tatsumi, M., Hirai, N., Mizoro, Y., et al. (2016). Cellular Adjuvant Properties, Direct Cytotoxicity of Re-generated Va24 Invariant NKT-like Cells from Human Induced Pluripotent Stem Cells. Stem Cell Reports 6, 213-227.

The prior art documents listed above are herein incorporated by reference.

SUMMARY OF INVENTION

In one aspect, an object of the present application is to provide a method for generating $CD4^-CD8^+$ T cells from pluripotent stem cells. More specifically, an object of the present application is to provide a method for generating $CD4^-CD8^+$ T cells having a desired antigen specific cytotoxic activity from pluripotent stem cells. Hereinafter, "CD8T cells" represents $CD4^-CD8^+$ T cells. In another aspect, an object of the present application is to provide a population of $CD4^-CD8^+$ T cells sharing the same antigen specificity and having a relatively high antigen specific cytotoxic activity.

In one aspect of the present application, provided is a method for preparing CD4⁻CD8⁺ T cells, comprising the steps of:
(1) preparing a cell culture comprising CD4⁻CD8⁻ T cells and CD4+CD8⁺ T cells by differentiating pluripotent stem cells,
(2) removing the CD4⁻CD8⁻ T cells from the cell culture obtained in step (1), and
(3) differentiating the CD4+CD8⁺ T cells in the cell culture obtained in step (2) into CD4⁻CD8⁺ T cells.

In another aspect, provided is a method for preparing CD4⁻CD8⁺ T cells, comprising the steps of:
(1) preparing a cell culture comprising CD4⁻CD8⁻ T cells and CD4+CD8⁺ T cells by differentiating pluripotent stem cells, and
(2) differentiating the CD4+CD8⁺ T cells in the cell culture obtained in (1) into CD4⁻CD8⁺ T cells under the presence of an agent that suppress the cytotoxic activity of the CD4⁻CD8⁻ T cells.

In the method of the present application, examples of pluripotent stem cells may include those having receptors specific for the desired antigen, for example, those having the rearranged T cell receptor (TCR) and the rearranged chimeric antigen receptor (CAR). CD4⁻CD8⁺ T cells induced from pluripotent stem cells bearing a rearranged TCR by the method according to this application exert antigen-specific cytotoxic activity with the same antigen specificity as the original TCR. The CD4⁻CD8⁺ T cells induced from pluripotent stem cells bearing a rearranged CAR are same as in the case of TCR.

Examples of pluripotent stem cells may also include those not having TCR and CAR. When they are used, CD4⁻CD8⁺ T cells exerting antigen-specific cytotoxic activity bearing the desired antigen specificity can be obtained by introducing the desired TCR in the CD4⁻CD8⁺ T cells induced from the pluripotent stem cells by a known method.

By the method of the present application, a cell culture wherein 80% or more, 85% or more, 90% or more or 95% more of the cells in the culture are CD4⁻CD8⁺ T cells sharing the same antigen specificity, especially the same TCR gene, can be prepared. The present application also provides thus obtained cell culture.

In another aspect, the present application provides a cell-based immunotherapy which comprises administering the antigen specific CD4⁻CD8⁺ T cells obtained by the method provided by this application to the subject in need of the therapy.

According to the present application, a cell culture comprising CD4⁻CD8⁺ T cells having a desired antigen specificity and relatively strong antigen-specific cytotoxic activity can be prepared.

DETAILED DESCRIPTION OF PREFERRED EMBODIMENTS

Figure 1:
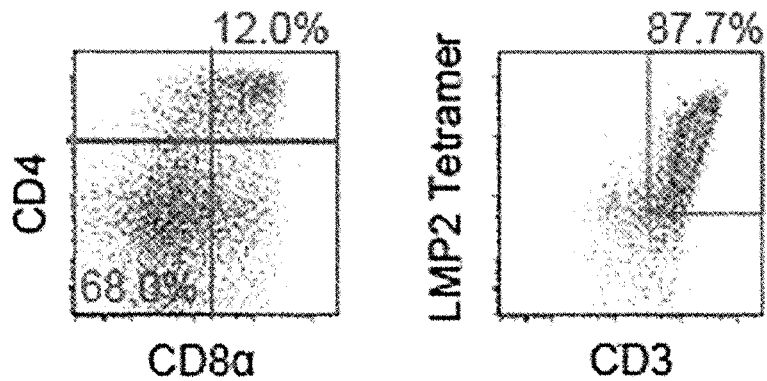
FIG. 1 shows a result of FACS analysis of a cell culture on day 35 of the conventional differentiation of LMP2 T-iPS cells into T cells.

In the specification and claims, the expression of "pluripotent stem cells" refers to stem cells having pluripotency, i.e. an ability to differentiate into many types of cells in the body, and self-propagation ability. Examples of pluripotent stem cells may include embryonic stem cells (ES cells), nuclear transfer embryonic stem cells (ntES cells), embryonic germ cells (EG cells), induced pluripotent stem cells (iPS cells), cultured fibroblasts and pluripotent cells derived from myeloid stem cells (Muse cells). Pluripotent stem cells are preferably mammalian cells and more preferably, human pluripotent stem cells, such as human ES cells and iPS cells. For creating a cell bank for the cell-based immunotherapy from human donors having specific HLAs, iPS cells are preferably used.

In the specification and claims, "T cells" refer to cells expressing receptors for antigens called as T cell receptor (TCR).

In the specification and claims, all of "CD4$^+$CD8$^+$ T cells", "double positive T cells" and "DP cells" represent CD4-positive CD8-positive T cells. All of "CD4$^-$CD8$^-$ T cells", "double negative T cells" and "DN cells" represent CD4-negative CD8-negative T cells. Unless otherwise indicated, "CD8T cells" include both CD8$\alpha\alpha$ homodimers and CD84 heterodimer. "TCR" means a T cell receptor. "CTL" means cytotoxic T lymphocyte.

T cells bearing a rearranged TCR with the desired antigen specificity may be obtained by establishing iPS cells from a T cell bearing the rearranged TCR which is specific for the desired antigen. The fact that a rearranged TCR of a T cell is maintained in iPS cells established from the T cell has been reported. See WO2011/096482 and Vizcardo et al., Cell Stem Cell 12, 31-36 2013, which is herein incorporated by reference. T cells used as origin for iPS cells may preferably be T cells expressing at least one of CD4 and CD8, in addition to CD3. Examples of preferable human T cells my include helper/regulatory T cells that are CD4 positive cells; cytotoxic T cells that are CD8 positive cells; naive T cells that are CD45RA$^+$CD62L$^+$ cells; central memory T cells that are CD45RA$^-$CD62L$^+$ cells, effector memory T cells that are CD45RA$^-$CD62L$^-$ cells and terminal effector T cells that are CD45RA$^+$CD62L$^-$ cells. Cytotoxic T lymphocytes (CTLs) are preferably used.

Human T cells can be isolated from a human tissue by known procedures. The human tissue is not limited in particular, as long as the tissue contains T cells of the above-mentioned type, and examples thereof may include peripheral blood, lymph node, bone marrow, thymus, spleen, umbilical cord blood, and a lesion site tissue. Among these, peripheral blood and umbilical cord blood are preferable since they can be derived less invasively from the human body and can be prepared with ease. Known procedures for isolating human T cells include, for example, flow cytometry using an antibody directing to cell surface markers, such as CD3, and a cell sorter. Alternatively, desired T cells can be isolated by detecting the secretion of a cytokine or the expression of a functional molecule as an indicator. In this case, for example, T cells secrete different cytokines, depending on whether they are of the Th1 or Th2 type, and thus T cells of a desired Th type can be isolated by selecting T cells using the cytokine as an indicator. Similarly, cytotoxic (killer) T cells can be isolated using the secretion or production of granzyme, perforin, or the like as an indicator.

Cytotoxic T lymphocytes specific for a cancer or infectious disease-associating antigen may be isolated from an individual who is suffered from said cancer or infectious disease or an individual who had previously been suffered from the cancer or infectious disease, and the cells may be proliferated. The antigen specific cytotoxic T lymphocytes may also be induced from cells obtained from a healthy volunteer.

Human T cells specific for a given antigen may be isolated from cell culture or tissue containing the antigen specific T cells with an affinity column immobilized with the desired antigen. Alternatively, tetramer of an antigen-bound major histocompatibility complex (MHC) may be used to isolate human T cells specific for the desired antigen specificity from human tissues.

Cytotoxic T lymphocytes specific for a given antigen may be induced by stimulating lymphocytes obtained from a human by a conventional procedure with the antigen or an epitope peptide thereof. Various antigen proteins or their epitope peptides specific for various diseases such as cancer, autoimmune disease or infectious disease have been known to the art. A suitable antigen or epitope peptide may be selected. The method for inducing CTLs by stimulating lymphocytes with an antigen has been well known to the art.

T cells having desired antigen specificity may also include CAR-T cells that are T cells bearing chimeric antigen receptor (CAR) obtained by means of gene engineering. CAR-T cells may be generated according to published procedures: Themeli, M. et al., Nat Biotechnol 31, 928-933 (2013) and Themeli, M. et al., Cell Stem Cell 16, 357-366 (2015), which are herein incorporated by reference.

iPS cells may be induced from thus obtained T cells specific for a desired antigen. The procedure for inducing pluripotent stem cells from T cells may be those taught by Vizcardo et al., Cell Stem Cell 12, 31-36 2013. For example, T cells specific for a given antigen may be obtained from an individual who had acquired immunity against the disease to be treated and the Yamanaka factors may be introduced to the T cells to give iPS cells (Takahashi and Yamanaka, Cell 126, 663-673 (2006), Takahashi et al., Cell 131, 861-872

(2007) and Grskovic et al., Nat. Rev. Drug Dscov. 10,915-929 (2011). The documents cited in this paragraph are herein incorporated by reference.

Induced pluripotent stem (iPS) cells can be prepared by introducing specific reprogramming factors to somatic cells. iPS cells are somatic cell-derived artificial stem cells having properties almost equivalent to those of ES cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106(2008); and WO 2007/069666). The reprogramming factors may be constituted by genes or gene products thereof, or non-coding RNAs, which are expressed specifically in ES cells; or genes or gene products thereof, non-coding RNAs or low molecular weight compounds, which play important roles in maintenance of the undifferentiated state of ES cells. Examples of genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tell, beta-catenin, Lin28b, Sall1, Sa114, Esrrb, Nr5a2, Tbx3 and Glisl, and these reprogramming factors may be used either individually or in combination. Examples of the combination of the reprogramming factors include those described in WO2007/069666; WO2008/118820; WO2009/007852; WO2009/032194; WO2009/058413; WO2009/057831; WO2009/075119; WO2009/079007; WO2009/091659; WO2009/101084; WO2009/101407; WO2009/102983; WO2009/114949; WO2009/117439; WO2009/126250; WO2009/126251; WO2009/126655; WO2009/157593; WO2010/009015; WO2010/033906; WO2010/033920; WO2010/042800; WO2010/050626; WO 2010/056831; WO2010/068955; WO2010/098419; WO2010/102267; WO 2010/111409; WO 2010/111422; WO2010/115050; WO2010/124290; WO2010/147395; WO2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26: 1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al. (2009), Nat. Biotech., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6: 167-74; Han J, et al. (2010), Nature. 463:1096-100; *Mali* P, et al. (2010), Stem Cells. 28:713-720, and Maekawa M, et al. (2011), Nature. 474: 225-9. The documents cited in this paragraph are herein incorporated by reference.

The reprogramming factors may be contacted with or introduced into the somatic cells by a known procedure suitable for the type of the factors to be used.

In the case where the reprogramming factors are protein, the reprogramming factors may be introduced into somatic cells by a method such as lipofection, fusion with a cell-permeable peptide (e.g., HIV-derived TAT or polyarginine), or microinjection.

In the case where the reprogramming factors are DNAs, the reprogramming factors may be introduced into somatic cells by means of a vector such as virus, plasmid and artificial chromosome vectors; lipofection; use of liposome; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (WO 2010/008054). Examples of the artificial chromosome vector include human artificial chromosome (HAC), yeast artificial chromosome (YAC), and bacterial artificial chromosome (BAC and PAC). Examples of the plasmid which may be used include plasmids for mammalian cells (Science, 322:949-953, 2008). The vector may contain a regulatory sequence(s) such as a promoter, enhancer, ribosome binding sequence, terminator and/or polyadenylation site to enable expression of the nuclear reprogramming factors; and, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG. Further, in order to remove, after introduction of the gene into the somatic cells and expression of the same, the genes encoding the reprogramming factors, or both the promoter(s) and the genes encoding the reprogramming factors linked thereto, the vector may have LoxP sequences upstream and downstream of these sequences. The documents cited in this paragraph are herein incorporated by reference.

Further, in the case where the reprogramming factors are RNAs, each reprogramming factor may be introduced into somatic cells by lipofection or microinjection, and an RNA into which 5-methylcytidine and pseudouridine (TriLink Biotechnologies) were incorporated may be used in order to suppress degradation (Warren L, (2010) Cell Stem Cell. 7:618-630). The documents cited in this paragraph are herein incorporated by reference.

Examples of the medium for inducing iPS cells include DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); and commercially available media [for example, medium for culturing mouse ES cells (TX-WES medium, Thromb-X), medium for culturing primate ES cells (medium for primate ES/iPS cells, ReproCELL) and serum-free medium (mTeSR, Stemcell Technology)].

Examples of the method to induce iPS cells include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for primate ES cells about 10 days after the contact between the somatic cells and the reprogramming factors, thereby allowing ES-like colonies to appear about 30 to about 45 days after the contact, or later.

Alternatively, the cells may be contacted with the reprogramming factors and cultured at 37° C. in a 5% $CO_2$ atmosphere on feeder cells (e.g., mitomycin C-treated STO cells or SNL cells) in DMEM medium supplemented with 10% FBS (this medium may further contain LIF, penicillin/streptomycin, puromycin, L-glutamine, non-essential amino acids, β-mercaptoethanol and the like, as appropriate) for about 25 to about 30 days or longer, thereby allowing ES-like colonies to appear. Preferred examples of the culture method include a method wherein the somatic cells themselves to be reprogrammed are used instead of the feeder cells (Takahashi K, et al. (2009), PLoS One. 4:e8067 or WO2010/137746), and a method wherein an extracellular matrix (e.g., Laminin-5 (WO2009/123349), Laminin-5 (WO2009/123349), Laminin-10 (US2008/0213885) or its fragment (WO2011/043405) or Matrigel (BD)) is used instead. The documents cited in this paragraph are herein incorporated by reference.

Other examples include a method wherein the iPS cells are established using a serum-free medium (Sun N, et al. (2009), Proc Natl Acad Sci U S A. 106: 15720-15725). Further, in order to enhance the establishment efficiency, iPS cells may be established under low oxygen conditions (at an oxygen concentration of 0.1% to 15%) (Yoshida Y, et al. (2009), Cell Stem Cell. 5:237-241 or WO2010/013845). The contents of the documents cited in this paragraph are herein incorporated by reference.

Examples of factors used for enhancing the establishment efficiency may include histone deacetylase (HDAC) inhibitors [e.g., low-molecular inhibitors such as valproic acid (VPA), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like], MEK inhibitor (e.g., PD184352, PD98059, U0126, SL327 and PD0325901), Glycogen synthase kinase-3 inhibitor (e.g., Bio and CHIR99021), DNA methyl transferase inhibitors (e.g., 5-azacytidine), histone methyl transferase inhibitors [for example, low-molecular inhibitors such as BIX-01294, and nucleic acid-based expression inhibitors such as siRNAs and shRNAs against Suv39h1, Suv39h2, SetDB1 and G9a], L-channel calcium agonist (for example, Bayk8644), butyric acid, TGF inhibitor or ALK5 inhibitor (e.g., LY364947, SB431542, 616453 and A-83-01), p53 inhibitor (for example, siRNA and shRNA against p53), ARID3A inhibitor (e.g., siRNA and shRNA against ARID3A), miRNA such as miR-291-3p, miR-294, miR-295, mir-302 and the like, Wnt Signaling (for example, soluble Wnt3a), neuropeptide Y, prostaglandins (e.g., prostaglandin E2 and prostaglandin J2), hTERT, SV40LT, UTF1, IRX6, GLIS1, PITX2, DMRTB1 and the like. Upon establishing iPS cells, a medium added with the factor for enhancing the establishment efficiency may be used.

During the culture, the medium may be replaced with the fresh medium once every day from Day 2 of the culture. The number of somatic cells used for nuclear reprogramming is not restricted, and usually within the range of about $5\times10^3$ to about $5\times10^6$ cells per 100 $cm^2$ area on the culture plate.

iPS cells may be selected based on the shape of each formed colony. In the cases where a drug resistance gene is introduced as a marker gene such that the drug resistance gene is expressed in conjunction with a gene that is expressed when a somatic cell was reprogrammed (e.g., Oct3/4 or Nanog), the established iPS cells can be selected by culturing the cells in a medium containing the corresponding drug (selection medium). Further, iPS cells can be selected by observation under a fluorescence microscope in the cases where the marker gene is the gene of a fluorescent protein. Thus induced iPS cells (T-iPS cells) bear genes encoding the T cell receptor (TCR) derived from the original T cell from which the iPS cells were induced.

In another embodiment according to this application, TCR genes specific for a desired antigen may be introduced into pluripotent stem cells to give pluripotent stem cells bearing genes encoding a T cell receptor specific for the desired antigen.

Cancer specific TCRs relating to various cancers have been reported. TCR genes may be isolated from T cells specific for a given antigen isolated from a patient having the cancer or induced from a healthy volunteer. TCR genes specific for a given antigen may include chimeric antigen receptor genes specific for the antigen.

The genes encoding a TCR specific for a desired antigen may be introduced into pluripotent stem cells such as iPS cells. For example, this procedure may be conducted as taught by Morgan R. A. et al, Science, 314:126. 2006. In particular, a suitable vector bearing the TCR genes may be introduced into the iPS cells. For example, TCR genes may be introduced by a vector such as virus, plasmid and artificial chromosome vectors; or by means of lipofection, liposome or microinjection. Examples of the virus vectors include retrovirus vectors, lentivirus vectors, adenovirus vectors, adeno-associated virus vectors and Sendai virus vectors. Examples of the artificial chromosome vector include human artificial chromosome (HAC), yeast artificial chromosome (YAC), and bacterial artificial chromosome (BAC and PAC). Examples of the plasmid which may be used include plasmids for mammalian cells. The vector may include a regulatory sequence(s) such as a promoter, enhancer, ribosome binding sequence, terminator and/or polyadenylation site to enable expression of the TCR genes. If desired, the vector may also contain a selection marker such as a drug resistance gene (e.g., kanamycin-resistant gene, ampicillin-resistant gene or puromycin-resistant gene), thymidine kinase gene or diphtheria toxin gene; and a reporter such as the green-fluorescent protein (GFP), β-glucuronidase (GUS) or FLAG.

In the method of the present application, pluripotent stem cells may be iPS cells induced from somatic cells other than T cells, or ES cells. In the specification and claims, the expression of "somatic cells" refers to any animal cells that are not germ-line cells or pluripotent cells such as a sperms, spermatocytes, ova, oocytes and ES cells. Somatic cells may preferably be mammalian cells including human cells. Examples of somatic cells may include fetal somatic cells, neonatal somatic cells, and somatic cells of mature healthy individuals or individuals with disease. In particular, examples of somatic cells may include differentiated cells, for example tissue stem cells (i.e. somatic stem cells) such as neural stem cells, hematopoietic stem cells, mesenchymal stem cells and dental pulp stem cells, tissue progenitor cells, lymphocytes, epithelial cells, endothelial cells, muscle cells, fibroblasts such as skin cells, hair cells, hepatocytes, gastric mucosa cells, enterocytes, splenocytes, pancreatic cells such as exocrine pancreatic cells, brain cells, lung cells and adipocytes. iPS cells may be induced from somatic cells by a method similar to the above method for inducing iPS cells from T cells.

The pluripotent stem cells bearing the genes encoding the desired TCR are differentiated into T cell population comprising DP cells and DN cells. The procedure for differentiating pluripotent stem cells into T cells may be that taught by Timmermans et al., Journal of Immunology, 2009, 182: 6879-6888, which is herein incorporated by reference.

In one embodiment, the pluripotent stem cells are co-cultured in with OP9 stromal cells, for example with a culture of mouse OP9 stromal cells to give hematopoietic progenitor cells. The obtained hematopoietic progenitor cells are then co-cultured with OP9/DLL1 cells. Upon co-culturing with OP9/DLL1 cells, the cell culture medium may be supplemented with IL-7, F1T-3L and SCF (Stem Cell Factor). When the pluripotent stem cells are differentiated by this procedure, a cell culture comprising both DN cells and DP cells can be obtained.

The inventors have found that when a cell mixture comprising DN cells and DP cells are stimulated with an anti CD3 antibody, DN cells kill DP cells. Accordingly, in the following step, the DN cells are removed from the cell culture. DN cells removed-cell culture may comprise substantially no DN cells and preferably, no more than 5%, no more than 3%, and especially less than 1% of DN cells. The step for removing DN cells from the cell culture comprising both DN and DP cells may be "enrichment of DP cells" and the DN cells-removed cell culture may be referred to as "enriched DP cell culture".

During the differentiation procedure from the pluripotent stem cells into T cells, the cell culture comprising DN cells and DP cells may also comprise CD8SP cells. The CD8SP cells may be CD8αα homodimer type T cells and therefore, CD8SP cells, especially CD8αα homodimer type T cells, are preferably removed simultaneously with removing the DN cells. The procedures for removing both DN cells and CD8SP cells are not limited. In one embodiment, DN cells and CD8SP cells can be removed by collecting CD4 positive cells by using a substrate to which anti CD4 antibody is attached, such as MACS beads. Further, CD8αα homodimer type T cells can be removed by collecting CD8SPαβ heterodimer type T cells by using a substrate to which CD8β is attached, such as MACS beads. In another embodiment, DN cells may be removed by collecting DN cells by using cell sorter to give a cell culture containing substantially no DN cells. Alternatively, a cell culture comprising substantially no DN cell or CD8SP cell may be prepared by collecting DP cells by means of a sell sorter. Further, a cell culture comprising substantially no CD8SPαα homodimer type T cells may be prepared by collecting CD8SPαβ heterodimer type T cells by means of a sell sorter.

The cells in the enriched DP cell culture are then differentiated into CD8SP cells. DP cells may be differentiated into CD8SP cells by directly activating any one of the activation pathways which occur upon stimulation of the T cell receptor. For example, T cells may be activated by adding PMA and Ionomysin, in a manner similar to TCR stimulation. Examples of procedures to stimulate TCR may include incubating DP cells in the presence of an anti-CD3 antibody. The culture medium may be supplemented with IL-7 and IL-2 in addition to the anti-CD3 antibody. The time period for culturing the cells in the culture medium comprising anti-CD3 antibody may be 3-10 days, for example 4-8 days or about 6 days.

When a DP cell culture is established from pluripotent stem cells bearing a receptor, for example a TCR, specific for the desired antigen, the DP cells can be differentiated into CD8SP cells by stimulating the cells with the antigen itself or antigen presenting cells that present said antigen. Similarly, when DP cells express a CAR, the DP cells can be differentiated into CD8SP cells by stimulating the cells with the antigen recognized by the CAR, for example, by adding the soluble antigen into the cell culture, by adding beads coated with the antigen into the cell culture, or by co-culturing the DP cells with cells that expressing the antigen.

Almost all of the CD8SP cells differentiated from the enriched DP cell culture by directly activating any one of the activation pathways which occur upon stimulation of the T cell receptor are CD8αβ type T cells, i.e. T cells expressing CD8αβ heterodimer. As revealed by the reference example 2 shown below, when a cell culture comprising DN cells and DP cells is subjected to the differentiation under the presence of anti-CD3 antibody without enriching the DP cells, almost all of the obtained cells were CD8αα homodimer. The CD8αα homodimer type T cells exert a relatively low antigen specific cytotoxic activity while a relatively high NK cell-like killing activity.

In another embodiment of the present application, the cell culture comprising both DN cells and DP cells may be differentiated by culturing the cells with the stimulation of anti-CD3 antibody in the presence of a substance that inhibits cytotoxic activity of the DN cells, without removing the DN cells. Examples of substances that inhibit cytotoxic activity of the DN cells may be a perforin inhibitor, a granzyme inhibitor, a Fas pathway inhibitor, a caspase inhibitor, and an inhibitory antibody against Natural Killer activating receptor.

The CD8SP cells differentiated from pluripotent stem cells bearing rearranged genes encoding the TCR or the CAR according to the method disclosed herein exert a potent cytotoxic activity. For example, when T-iPS cells are established from a human CTL cell and then, the T-iPS cells are differentiated into CD8SP cells (re-generated CTLs) through the step of enrichment of the DP cells, re-generated CTLS that exert antigen specific CTL activity comparative to that of the original CTLs from which the T-iPS cells were established can be prepared. Further, when pluripotent stem cells bearing rearranged genes encoding the TCR or the CAR are used, the Rag1 or Rag2 gene in the pluripotent stem cells may be knocked out by genome editing before differentiating the pluripotent stem cells into T cells to prevent re-arrangement of the TCR or CAR genes (WO2016/010148). Methods for generating pluripotent stem cells bearing genes encoding a CAR which is specific for a given antigen, and method for differentiating said pluripotent stem cells into CAR-expressing T cells are taught in, for example, Themeli, M. et al., Nat Biotechnol 31, 928-933 (2013) and Themeli, M. et al., Cell Stem Cell 16, 357-366 (2015). The contents of those documents are herein incorporated by reference.[0052]

In yet another embodiment of the present application, cytotoxic T lymphocytes specific for a desired antigen may be obtained by expressing the TCR gene with desired antigen specificity on the CD8SP cells differentiated from pluripotent stem cells. In this embodiment, the pluripotent stem cells may have TCR or CAR genes, or may not have those genes. TCR genes specific for a desired antigen may be expressed in the CD8SP cells by a method similar to the method for expressing the TCR genes specific for a desired antigen in the pluripotent stem cells. Upon expressing said TCR, the endogenous TCR genes in the generated CD8SP cells may be suppressed by means of, for example, siRNA.

Alternatively, T cells bearing chimeric antigen receptor (CAR) specific for a desired antigen (CAR-T cells) may be generated from the CD8SP cells. The CAR-expressing cells can be obtained by introducing genes encoding the CAR into the CD8SP cells.

The antigen specific CTLs prepared according to the method provided herein may be proliferated by a known method, for example by stimulating the cells with the antigen itself or antigen presenting cells that present said antigen, or with anti-CD3 antibody before use.

There are a lot of cancer relating proteins that are expressed in a variety of cancers including LMP2, WT1 and NY-ESO1. Epitope peptides of those proteins are also known to the art as cancer antigen peptides and may be used in the method of this application. In addition, many genes encoding TCRs specific for various cancer antigens are also known to the art. By the method of the present application, it becomes possible to obtain a cell population containing high quality CD8SP cells having cytotoxic activity specific for a given cancer antigen with high purity, which is useful in the cell-based immunotherapy.

As shown by the examples provided in this application, therapeutic effect of the CD8SP cells obtained by the method in a human tumor-inoculated mouse model was confirmed. In addition, in the mice administered with the re-generated CD8SP cells, no damage in tissues other than the tumor was observed and no adverse effect was observed. Further, canceration of the in vivo administered cells was not observed. The re-generated cells prepared according to the method of the present application are expected to be used in a cell-based immunotherapy in which CTLs specific for a cancer or infections disease-specific antigen are administered to a patient. Both efficacy and safety points of view, The re-generated cells are considered to be close to clinically applicable.

According to this application, T cell products for use in immunotherapies targeting various antigens can be provided. For example, cytotoxic T lymphocytes (CTLs) specific for a given antigen can be induced from cells of a healthy volunteer, T-iPS cells can be established from the CTLs, and CD8SP cells can be re-generated from the T-iPS cells. The function of thus re-generated CD8SP cells may be confirmed and then, the T-iPS cells may be stored to create a T-iPS bank. Alternatively, the re-generated CD8SP cells may be proliferated and stored in aliquots.

The HLA of the patient with a cancer expressing the target antigen may be determined and HLA-matched T-iPS cells may be chosen from the T-iPS cell bank. Then, CD8SP cells may be re-generated from the T-iPS cells according to the method of the present application and used for the cell-based immunotherapy. Alternatively, suitable CD8SP cells may be selected from the stored re-generated cells. By the latter procedure, a cell-based immunotherapy can be started more quickly.

In the cell-based immunotherapy method of the present application, the induced CD8SP cells are dispersed in a suitable media such as saline or PBS and the dispersion may be administered to a patient having a certain matching level of the HLA to the donor. The matching level of the donor and the patient may be complete match. When the donor is homozygous for HLA haplotype (hereinafter referred to as "HLA haplotype homo") and the patient is heterozygous for HLA haplotypes (hereinafter referred to as "HLA haplotype hetero"), one of the patient's HLA haplotypes should match the donor's homozygous HLA haplotype. The cells may be administered intravenously. The amount of the cells to be administered is not limited. Cells that have been differentiated into mature T cells may be intravenously administered once to several times in an amount of $10^6$-$10^7$ cells/kg body weight per administration.

A project to construct a versatile iPS cell bank is now in progress in Japan by using a human having a frequent HLA haplotype in homozygous as the donor. See, CYRANOSKI, Nature vol. 488, 139(2012), which is herein incorporated by reference. When CD8SP cells for the cell-based immunotherapy method are established according to the method of the present application, iPS cells which are induced from cells derived from such donor homozygous for HLA haplotype are particularly preferably used, as pluripotent stem cells.

The number of the cells to be administered is not limited and may be determined based on, for example, the age, sex, height and body weight of the patient and disease and conditions to be treated. The optimal cell number may be determined through clinical studies. T cells may target various antigens and therefore, the method of this application may be applied for a cell-based immunotherapy against various diseases including cancers, infectious diseases, autoimmune diseases and allergies.

Reference Example 1

Establishment of iPS Cells
Preparation of Peripheral Blood Mononuclear Cells, Auto LCL Cell Line and CIR-A*24:02 Cell Line Peripheral blood mononuclear cells (PBMC) were isolated from a healthy volunteer having HLA-A*24:02, and bone marrow mononuclear cells were isolated from a leukemia patient according to the conventional procedure. The peripheral blood B lymphocytes were transformed with Epstein Barr virus (EBV) to give autologous B-lymphoblastoid cell line (auto). HLA-A*24:02 gene was introduced into human LCL cell line, C1R cells to give C1R-A*24:02 cell line that expresses only HLA A*24:02.

Proliferation of LMP2 and WT1 Peptide Specific CTLs

PBMCs obtained from the healthy volunteer ($2.5 \times 10^5$ cells) were added to each well of a 96-well round bottom plate and incubated in RPMI 1640 medium added with 10% human AB serum (Sigma), penicillin (100 U/mL)-streptomycin (100 μg/mL) mixed solution (Nacalaitesque) and 10 μg/mL of a LMP2 specific synthetic peptide (TYGPVFMSL: SEQ ID No. 1) or a WT1 specific synthetic peptide (CYTWNQMNL: SEQ ID No. 2) (Eurofins) (Tsuboi, A et al. (2002) Cancer Immunol Immunother. 51, 614-620). Two days after the incubation, recombinant IL-2, (12.5 U/ml) (Peprotech), IL-7 (10 ng/ml) (Peprotech) and IL-21 (30 ng/ml) (Peprotech) were added to each well.

CD8 positive T cells containing antigen specific CTLs were isolated by means of the tetramer staining procedure. The isolated CD8 positive cells were co-cultured with HLA-A*24:02-positive LCLs previously incubated in the presence of 100 nM of the LMP2 or WT1-specific synthetic peptide and irradiated. The cell mixture were incubated for 2 days and then, added with the same concentration of IL-2, IL-7 and IL-21 as above. CTLs were proliferated by stimulating the cells with the LCLs every two weeks. Thus obtained CTLs are referred to as "Original CTLs".

Establishment of LMPs or WT1 specific iPSCs.

Cancer antigen specific T-iPS cells were established according to a protocol slightly modified from that disclosed in Non-patent literature 1. Briefly, the cancer-antigen specific CTLs were enriched with CD8 micro beads (Milteny Biotec) or FACSAria III cell sorter (BD Biosciences). The enriched cancer antigen specific CTLs ($1 \times 10^6$ cells) were transfected with a Sendai virus vector bearing the four Yamanaka factors and SV40 large T antigen (LTa) (Addgene) (MOI MOI=3) (Nishimura, K. et al., (2011) J Biol Chem 286, 4760-4771). After spin infection, the transformed cells were inoculated on the mouse embryonic fibroblast (MEF) feeder cells and incubated in a T-cell medium, i.e. RMPI-1640 medium supplemented with IL-7 (10 ng/mL) and IL-21 (30 ng/mL). On day 2, a half of the medium was replaced with a medium for human iPS cells, i.e. Dulbecco's Modified Eagle's Medium supplemented with 20% KnockOut™ Serum Replacement (Gibco), non-essential amino acids (0.1 mM) Gibco), 2-mercaptoetanol (blood supplement mM) (Nacalai Tesque) and basic fibroblast growth factor (5 ng/mL) (Wako). Colonies started to appear on the 21st-35th day. Each of the colonies was picked up and proliferated.

Each one of T-iPS cell clones established from the LMP2 specific T cells and from the WT1 specific CTLS was selected and was subjected to the following experiments. Colonies are represented as "LMP2-T-iPS cells" and "WT1-T-iPS cells" respectively.

Induction of the T-iPS Cells into CD8SP Cells by a Conventional Procedure

Figure 2:
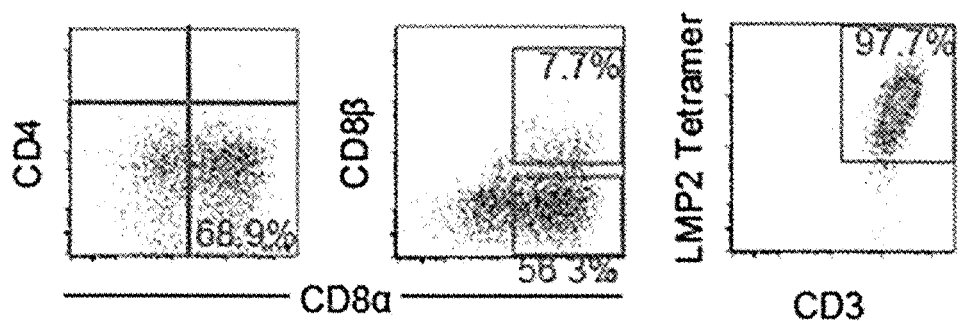
FIG. 2 shows a result of FACS analysis of a cell culture obtained by incubating the cells of FIG. 1 under the stimulation of anti-CD3 antibody for 6 days.

LMP-T-iPS cells obtained in Reference Example 1 were induced into T cells according to the protocol taught in Non-Patent Literature 1. Until Day 35 of the induction, the procedure was the same as Example 1 shown below. On day 35 of the induction, the cells were subjected to FACS analysis. In the cell culture comprising the LMP2 antigen specific T cells, the proportion of DP cells was 12.0% and that of DN cells was 68.0% (FIG. 1). The cell culture was incubated under the stimulation of anti CD3 antibody for 6 days to give a cell culture containing 68.9% of CD8SP cells. The obtained CD8SP cells were specific for LMP2 tetramer and almost all were CD8αα homo-dimer type T cells (FIG. 2). Genes encoding TCR of the obtained cells were confirmed to be identical to those of the original LMP2 specific CTL (Data not shown). Hereinafter, thus obtained cells are referred to as "Re-generated CTLs".

Figure 3:
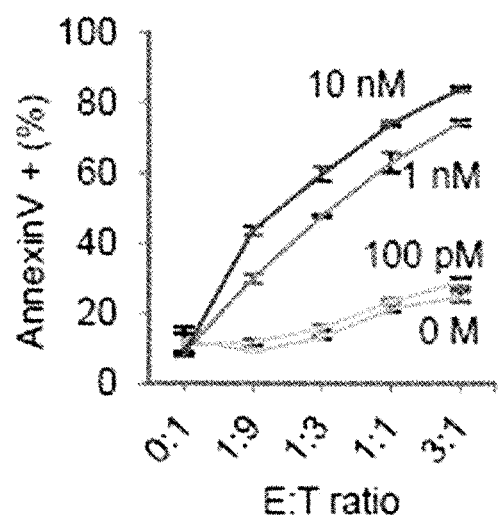
FIG. 3 is a graph showing the peptide-specific cytotoxic activity of the CTLs from which the LMP2-T-iPS cells were established.
Figure 4:
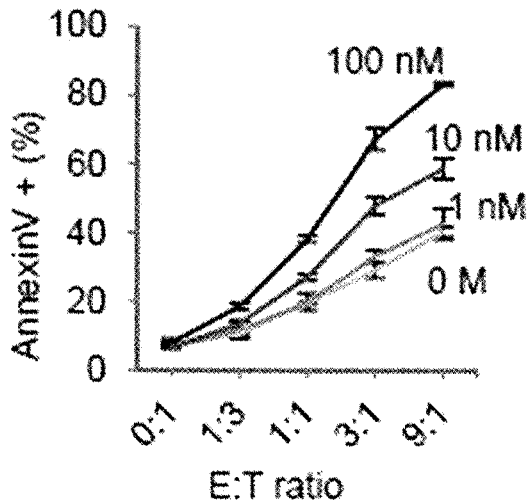
FIG. 4 is a graph showing the peptide-specific cytotoxic activity of the CD8SP cells re-differentiated from the LMP2-T-iPS cells by the conventional procedure.
Figure 5:
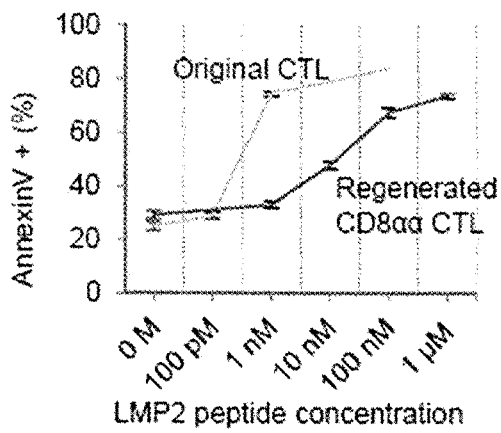
FIG. 5 is a graph that compares the peptide specific cytotoxic activities of the CD8SP cells (re-generated CTLs) that were re-generated from the LMP2-T-iPS cells by the conventional procedure and of the original CTLs from which the LMP2-T-iPS cells were established.

The peptide-specific cytotoxic activities of the original LMP2 specific CTLs and the re-generated CTLs were determined using LMP2 peptide pulsed THP1 cells, i.e. cells of a HLA A*24:02 positive human leukemia cell line. The CTLs and the leukemia cell line were mixed so that the Effector: Target (E:T) ratio is 0:1, 1:9, 1:3, 1:1, 3:1 and 9:1 and the mixed cells were incubated at 37° C. in a 5% $CO_2$ atmosphere for 6 hours. Cytotoxic activities were evaluated based on the ratio of Annexin V positive cells. Results are shown in FIGS. 3 and 4. In addition, the cytotoxic activities of both cells when ET ratio was 3:1 are shown in FIG. 5. The peptide specific cytotoxic activity of the re-generated CTLs was about 1/100 of the original CTLs.

Figure 6:
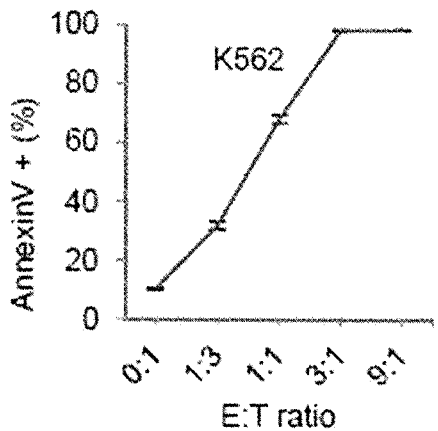
FIG. 6 shows natural killer cell-like activities of the CD8SP cells (re-generated CTLs) that were re-generated from LMP2-T-iPS cells by the conventional procedure.

In addition, the NK cell-like cytotoxic activity of the re-generated CTLs against the K562 cells was evaluated. Result is shown in FIG. 6. The re-generated CTLs had confirmed to have a relatively high NK cell-like cytotoxic activity.

Example 1

Figure 7:
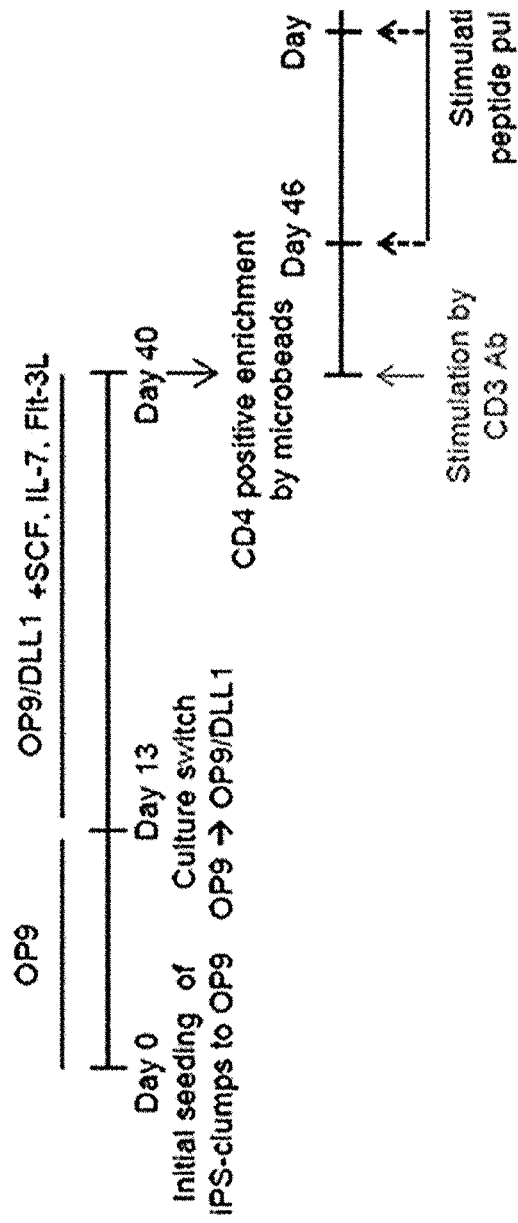
FIG. 7 shows procedure of Example 1 for differentiating pluripotent stem cells into T cells.

LMP2-T-iPS cell clone obtained in reference example 1 was used. T cells were re-generated from the T-iPS cells according to the procedure explained in FIG. 7.

1) Differentiation from T-iPS cells into a cell population comprising DP cells and DN cells.

Media used are as follows:

TABLE 1

| Medium A: for maintenance of OP9 stromal cells | | |
|---|---|---|
| contents | amount added | final conc. |
| αMEM medium | 500 mL | |
| FCS | 125 mL | 20% |
| penicillin-streptomycin solution* | 6.25 mL | 1% |
| Total | 631.25 mL | |

*Mixture of Penicillin (10,000 U/ml) and Streptomycin (10,000 µg/ml). The final concentrations were 100 U/ml and 100 µg/ml, respectively.

TABLE 2

| Medium B: for inducing differentiation of T cells No. 1 | | |
|---|---|---|
| contents | amount added | final conc. |
| Medium A | 50 mL | |
| hrIL-7 (stock: 10 µg/mL) | 25 µL | 5 ng/mL |
| hrFlT-3L (stock: 10 µg/mL) | 25 µL | 5 ng/mL |
| hrSCF (stock: 10 µg/mL) | 25 µL | 5 ng/mL |
| Total | 50.75 mL | |

*Mixture of Penicillin (10,000 U/ml) and Streptomycin (10,000 µg/ml). The final concentrations were 100 U/ml and 100 µg/ml, respectively.

TABLE 3

| Medium C: for inducing from immature T cells into mature T cells | | |
|---|---|---|
| contents | amount added | final conc. |
| medium A | 50 mL | |
| hrIL-7 (stock: 10 µg/mL) | 25 µL | 5 ng/mL |
| hrFlT-3L (stock: 10 µg/mL) | 2.5 µL | 0.5 ng/mL |
| hrSCF (stock: 10 µg/mL) | 2.5 µL | 0.5 ng/mL |
| Total | 50.03 mL | |

*Mixture of Penicillin (10,000 U/ml) and Streptomycin (10,000 µg/ml). The final concentrations were 100 U/ml and 100 µg/ml, respectively.

Preparation of OP9 Cells

Five milliliters (5 mL) of 0.1% gelatin solution in PBS was added to a 10 cm dish (Falcon) and incubated for 30 minutes at 37° C. OP9 stromal cells were detached from a confluent culture dish with trypsin/EDTA solution and about ¼ of the obtained cells were added to the gelatin-coated 10 cm cell culture dish. 10 mL of medium A was added to the cell culture dish.

Four days after, 10 mL of medium A was added to the dish (final amount was 20 mL).

Preparation of OP9/DLL1 Cells in 24-Well Plate

OP9/DLL1 cells were detached from a confluent culture dish with trypsin/EDTA solution and about ¼ of the obtained cells were suspended in 12 mL of medium A and 0.5 mL of the suspension was seeded in each well of a 24-well plate. Two days after the seeding, the plate was used as OP9/DLL1 cell culture plate.

Induction from T-iPS cells into hematopoietic progenitor cells.

iPS cell colonies were detached from the T-iPS cell culturing dish (6 cm dish) with a detaching solution and were mechanically fragmented to smaller sizes by means of pipetting. The fragmented cell masses were then centrifuged at 1200 rpm for 5 minutes at 4° C. The obtained pellet was suspended in 10 mL of medium A. The fragmented iPS cell masses obtained from one 6 cm dish was seeded on the previously prepared OP9 cell dish.

Day 1: (the Medium was Replaced)

Whether the iPS cell masses were adhered to the dish and started to differentiate were confirmed. The cell culture medium was replaced with 20 mL of fresh medium A.

Day 5: (a Half of the Medium was Replaced)

A half of the cell culture medium was replaced with 10 mL of fresh medium A.

Day 9: (a Half of the Medium was Replaced)

A half of the cell culture medium was replaced with 10 mL of fresh medium A.

Day 13: (Induced Mesodermal Cells were Transferred from OP9 Cell Layer onto OP9/DLL1 Cell Layer)

Cell culture medium was aspirated to remove and the surface of the cultured cells were washed with HBSS (+Mg+Ca) to washout the cell culture medium. 6 mL of Collagenase IV 250U in HBSS (+Mg+Ca) solution was added to the dish and incubated for 45 minutes at 37° C.

The collagenase solution was removed by aspiration and the cells were washed with 10 mL of PBS(−). Then, 2 mL of 0.05% trypsin/EDTA solution was added to the dish and the dish was incubated for 25 minutes at 37° C. After the incubation, the sheet like cell aggregates peeled from the bottom of the dish and the cell aggregates were mechanically fragmented to smaller sizes by means of pipetting. Thus treated cells were added with fresh medium A 8 mL and cultured for more 45 minutes at 37° C.

The culture medium containing the floating cells was passed through a 70 µm mesh and the cells were collected. The cells were then centrifuged at 1200 rpm for 5 minutes at 4° C. The obtained pellet was suspended in 10 mL of medium B. One-fifth of the suspension was separated and used for the FACS analysis. The remaining cell suspension was seeded to new dishes containing OP9/DLL1 cells. Cell suspensions obtained from several dishes were pooled and the pooled cells were seeded to the same number of new dishes.

Figure 8:
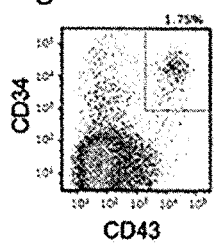
FIG. 8 shows a result of FACS analysis of the cell culture on day 13 of the differentiation of pluripotent stem cells into T cells in Example 1.

In order to ascertain whethher or not hematopoietic progenitor cells were contained in the obtained cells (FACS analysis was carried out using anti-CD4 antibody and anti-CD 43 antibody. When a sufficient number of cells could be confirmed in the CD34lowCD43+ cell fraction, it was determined that hematopoietic progenitor cells were induced (FIG. 8).

Day 15: (Cells were Subcultured)

The cells loosely adhered to the OP9 cells were dissociated by gently pipetting several times and collected in a 50 mL conical tube. The tube was centrifuged at 1200 rpm for 5 minutes at 4° C. The pellet was dispersed in 10 mL of medium B. Thus prepared cell suspension was seeded on the freshly prepared OP9/DLL1 cells. Cell suspensions obtained from 2-3 10 cm dishes were pooled in one dish.

Day 22: (Cells were subcultured) Blood cell colonies began to appear.

The cells loosely adhered to the OP9/DLL1 cells were dissociated by gently pipetting several times and collected in a 50 mL conical tube. The tube was centrifuged at 1200 rpm for 5 minutes at 4° C. The pellet was dispersed in 10 mL of medium B and seeded on the freshly prepared OP9/DLL1 cells.

Day 29: (Cells were Subcultured)

The cells loosely adhered to the OP9/DLL1 cells were dissociated by gently pipetting several times and collected in a 50 mL conical tube. The tube was centrifuged at 1200 rpm for 5 minutes at 4° C. The pellet was dispersed in 10 mL of medium C and seeded on the freshly prepared OP9/DLL1 cells.

Day 36: (Cells were Subcultured)

The cells loosely adhered to the OP9/DLL1 cells were dissociated by gently pipetting several times and collected in a 50 mL conical tube. The tube was centrifuged at 1200 rpm for 5 minutes at 4° C. The pellet was dispersed in 10 mL of medium C and seeded on the freshly prepared OP9/DLL1 cells.

Enrichment of DP Cells (Removing DN Cells and CD8SP Cells)

The following media were used:

TABLE 4

| MACS buffer | | final conc. |
|---|---|---|
| PBS | 50 mL | |
| BSA (stock: 10%) | 500 µL | (0.1%) |
| Total | 50.5 ml | |

TABLE 5

Medium D for differentiating into CD8SP cells

| | | final conc. |
|---|---|---|
| medium A | 50 mL | |
| hrIL-7 (stock: 10 µg/ml) | 25 µL | 5 ng/mL |
| hrIL-2 (stock: 10000 U/ml) | 50 µL | 100 U/mL |
| CD3Ab (stock: 1 mg/ml) | 0.7 5 µL | 15 ng/mL |
| Total | 50.07575 mL | |

Day 40: Enrichment of DP Cells (Removing DN Cells and CD8SP Cells)

Figure 9:
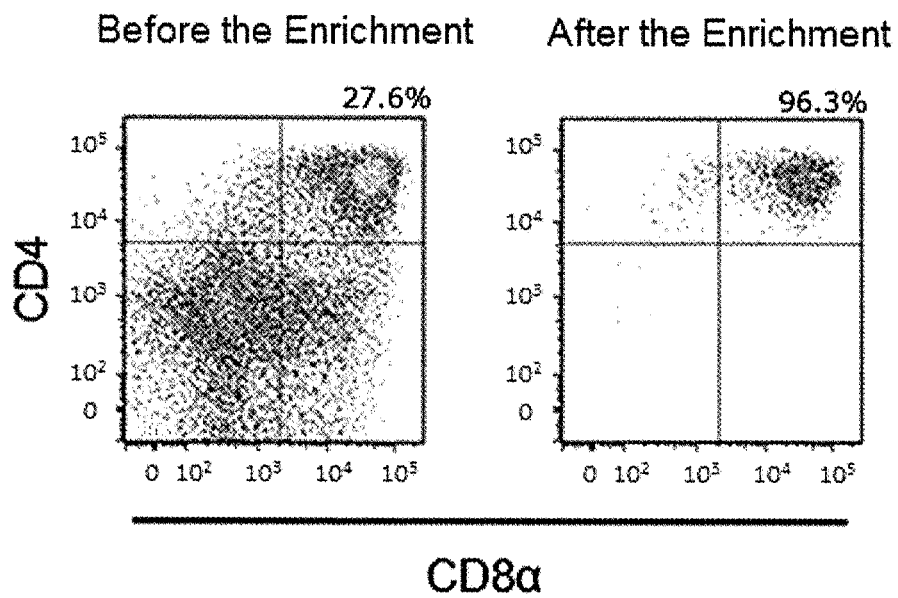
FIG. 9 shows a result of FACS analysis of the cell cultures on day 40 of the differentiation from pluripotent stem cells into T cells in Example 1, before and after the enrichment of the DP cells.

The cells loosely adhered to the OP9/DLL1 cells were dissociated by gently pipetting several times and collected in a 50 mL conical tube. The tube was centrifuged at 1200 rpm for 5 minutes at 4° C. The pellet was dispersed in 180 µL of MACS buffer. Anti CD4 antibody-attached MACS beads 20 µL were added and incubated for 15 minutes at 4° C. CD4 positive cells were collected according to the MACS protocol using the MACS column. The CD4/CD8 patterns of the cells before and after the enrichment were analyzed by FACS. Results are shown in FIG. 9. Before the enrichment, 27.6% of DP cells, 51.8% of DN cells and 18.4% of CD8SP cells were contained in the culture and after the enrichment, a cell culture containing 96.3% of DP cells, 0.263% of DN cells and 0.072% of CD8SP cells was obtained.

Induction of CD8αβSP Cells from Cells in the Enriched DP Cell Culture

Figure 10:
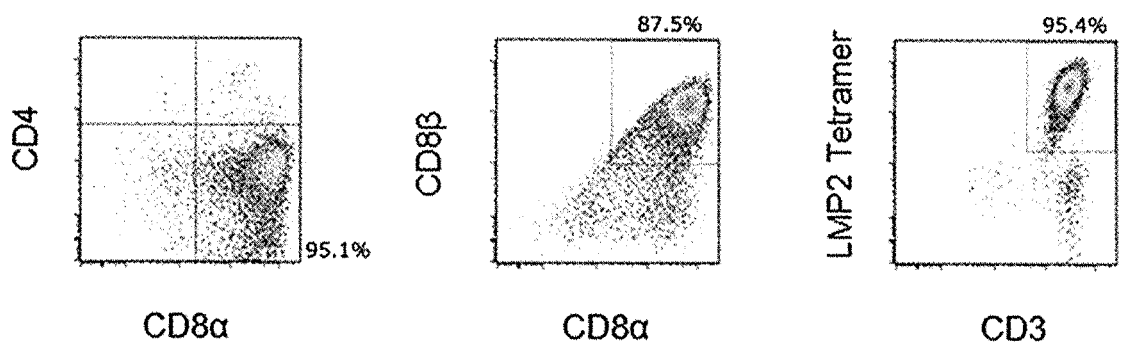
FIG. 10 shows a result of FACS analysis of the CD8SP cells induced by stimulating cell culture enriched for DP cells with anti-CD3 antibody. The cell culture in Example 1 was enriched for DP cells on day 40 of the differentiation before the stimulation by anti-CD3 antibody. The cells were LMP2 antigen specific and CD8αβ type T cells.

The enriched DP cell culture was dispersed in medium D to give a cell suspension at a final concentration of 5×10⁵ cells/mL. Medium in the previously prepared OP9/DLL1 cell culture dish was removed by aspiration, 1 m/well of the cell suspension was seeded on the OP9/DLL1 cell layer and incubated for 6 days. After 6 days incubation, the cells were collected and subjected to the FACS analysis. Results are shown in FIG. 10.

In the cell culture, the percentage of CDSP cells was 95.3%. The CD8SP cells were subjected to FACS analysis and confirmed that 87.5% of the obtained CD8SP cells were CD8αβ type T cells. Hereinafter, thus obtained cells are referred to as "re-generated CD8αβSP cells".

On the other hand, DN cells were also enriched on Day 40 to give a cell culture containing about 99% DN cells was obtained. The obtained enriched DN cell culture was stimulated with anti CD3 antibody for 6 days in the same manner as above. As a result, LMP2 tetramer positive cells, CD3 positive CD8SP cells were obtained. However, about 87% of the obtained CD8SP cells were CD8αα type T cells.

Proliferation of the Re-generated CD8αβSP cells.

The re-generated CD8αβSP cells were proliferated by antigen presenting cells (APC) presenting the LMP2 antigen.

TABLE 6

| x2 medium E for proliferation into CD8SP cells | | |
|---|---|---|
| | final conc. | |
| medium A | 50 mL | |
| hrIL-7 (stock: 10 µg/ml) | 50 µL | 10 ng/mL |
| hrIL-21 (stock: 10 µg/ml) | 100 µL | 20 ng/mL) |
| Total | 50.15 mL | |

Preparation of the Antigen Presenting Cells (APC)

The autologous LCLs were incubated in the presence of the LMP2 antigen peptide: TYGPVFMSL (SEQ ID No.1) and used as APCs. LCLs were collected from the culture bottle and irradiated at a dose of 50Gy. The cells were centrifuged at 1200 rpm for 5 minutes at 4° C. The obtained pellet was dispersed in medium A to give $5\times10^6$ cells/ml cell suspension. The peptide was added to give the final concentrations of 10 nM and the cells were incubated for 2 hours at 37° C.

Stimulation of the Re-Generated CD8αβSP Cells with the APC

The peptide added LCLs prepared above were centrifuged at 1200 rpm for 5 minutes at 4° C. The obtained pellet was dispersed in medium A to give $4\times10^5$ cells/ml cell suspension. The re-generated CD8αβSP cells were also centrifuged 1200 rpm for 5 minutes at 4° C. The obtained pellet of re-generated CD8αβSP cells was dispersed in x2 medium E to give a $1\times10^6$ cells/mL cell suspension. Each 0.5 ml of the peptide-stimulated LCLs suspension and the CD8αβSP cell suspension were co-cultured.

Figure 11:
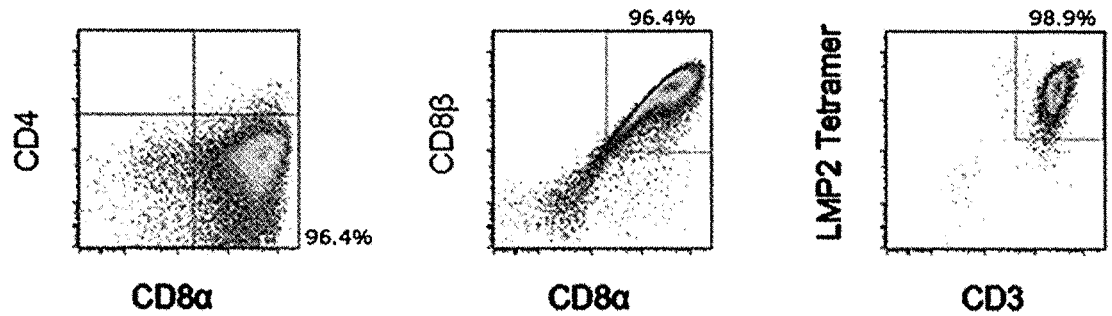
FIG. 11 shows a result of FACS analysis of the CD8SP cells in FIG. 10 further proliferated in the presence of the LMP2 antigen pulsed antigen presenting cells (APC).
Figure 12:
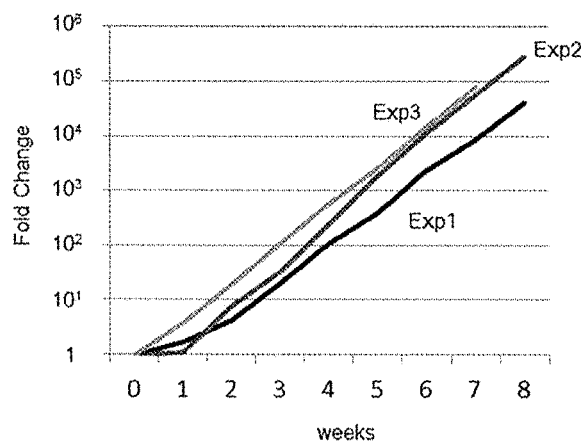
FIG. 12 shows cell growth curve of the CD8SP cells in FIG. 10 further proliferated in the presence of the LMP2 antigen pulsed antigen presenting cells (APC).

FACS patterns of the cells on day 14 of the co-culture are shown in FIG. 11. From day 7, the medium was replaced with the freshly prepared medium and the cells were proliferated by stimulating the cells every 7-14 days. The experiments were 3 times and the proliferation curves are shown in FIG. 12.

Figure 13:
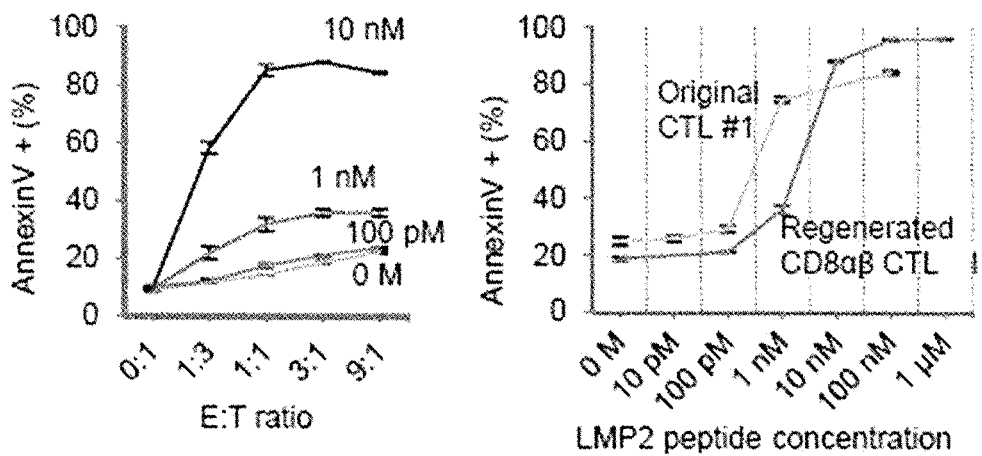
FIG. 13 (left) is a graph showing the peptide specific cytotoxic activity of the re-generated CD8SP cells (re-generated CD8αβ cells). The right figure is a graph in which the peptide specific cytotoxic activities of the original CTLs from which the LMP2-T-iPS cells were generated and the re-generated CD8SP cells are compared.

The antigen specific cytotoxic activity of the re-generated CD8αβSP cells was tested in the same manner as Reference Example 2. Results are shown in FIG. 13. In addition, the cytotoxic activities at the E:T ratio of 3:1 of the CD8αβSP cells and the original CTLs were compared. Results are shown in FIG. 13. The regenerated CD8αβSP cells or regenerated CD8αβ CTL cells exerted peptide specific cytotoxic activity comparative to that of the original CTLs.

Reference Example 3

Co-Culture of the DP Cells and DN Cells

Figure 14:
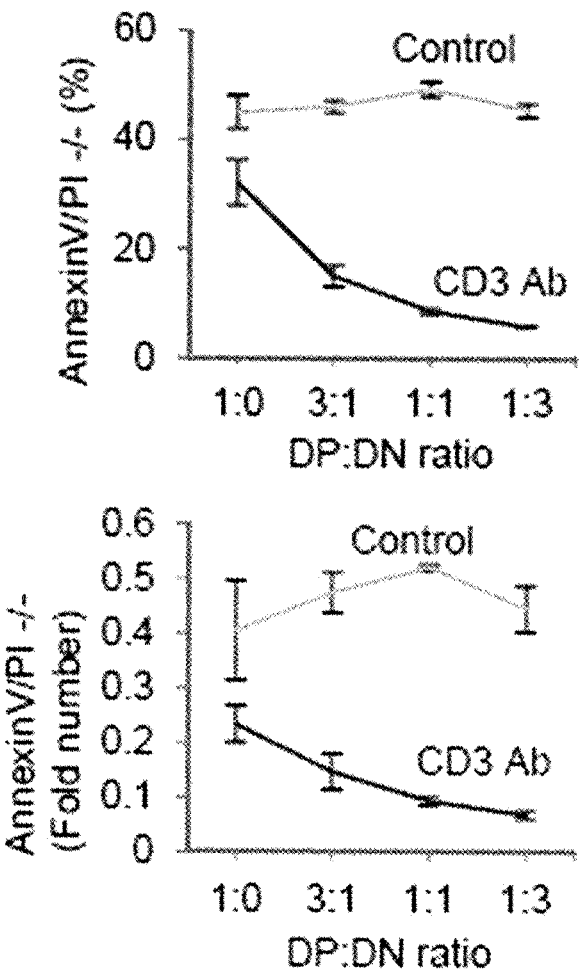
FIG. 14 are graphs showing the percentages of the viable cells among the DP cells after the incubation (upper) and before the incubation (lower). On day 40 of the differentiation of the iPS cells into T cells, T cells were divided into DP cells and DN cells. Then, DP cells and DN cells were mixed so that the DP:DN ratio was 1:0, 3:1, 1:1 and 1:3, and the mixed cells were incubated in the presence of anti-CD3 antibody for 5 hours.

According to the same protocol as Example 1, cells of the LMP2-T-iPS clone obtained in reference example 1 were incubated until day 40. The obtained cell culture was sorted into DP cells and DN cells. DP cells and DN cells were labelled with Cell Trance Violet and CFSE, respectively. The purity of both DP cell population and DN cell population were more than 99%. $3\times10^4$ of the DP cells were mixed with DN cells to give DP:DN ratio of 1:0, 3:1, 1:1 and 1:3 and then, incubated in the presence or absence of anti CD3 antibody for 5 hours. Thus obtained cells were stained with Annexin V and PI (Propidium Iodide) and the Annexin V-negative and PI-negative cell fraction was determined as viable cells. Viable cells among the Violet positive cells, i.e. DP cells and viable cells among the DP cells at the start of the co-culture are shown in FIG. 14. It was shown that the DN cells killed DP cells under the stimulation of anti CD3 antibody.

Example 2

WT1 Peptide Specific Cytotoxic Activity of WT1 Specific CD8SP Cells

Re-generated CD8SP cells were induced from the WT1-T-iPS cells obtained in the reference example 1. On day 40 of the differentiation, an enriched DP cell culture containing 84.7% of DP cells was obtained. The obtained enriched DP cell culture was stimulated by CD3 Ab to give a cell culture containing the re-generated CD8SP cells. 89.2% of the CD8SP cells in thus obtained re-generated CD8SP cell culture were CD8αβ type T cells. WT1 specific cytotoxic activity of the re-generated CD8SP cells was evaluated.

Figure 15:
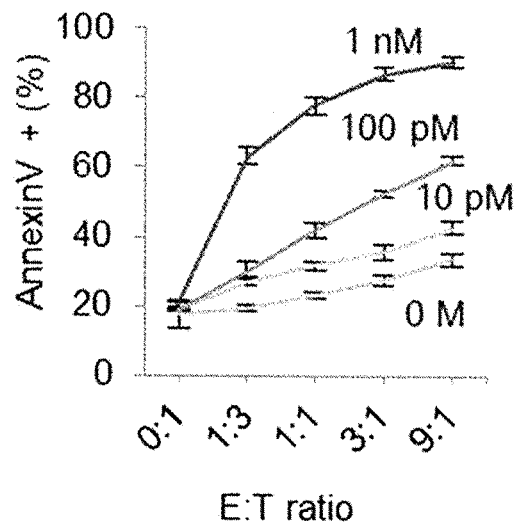
FIG. 15 is a graph showing the WT1 peptide specific cytotoxic activity of the CD8SP cells induced from WT1-T-iPS cells according to the procedures shown in FIG. 7.

C1R A*24:02 (human LCL cell line) was incubated under the presence of various concentration of the WT1 peptide, CYTWNQMNL (SEQ ID No.2) for 2 hours. C1R A*24:02 cells were collected from each culture and mixed with the CD8SP cells to give E:T ratio of 0:1, 1:3, 1:1, 3:1 and 9:1. The cell mixture was incubated for 6 hours at 37° C. in a 5% $CO_2$ atmosphere. After that, cytotoxic activity was determined by the ratio of Annexin V positive cells. Results are shown in FIG. 15.

The cytotoxic activity increased depending on the peptide concentration and the cell number. The re-generated CD8SP cells were confirmed to have WT1 antigen specific cytotoxic activity.

Figure 16:
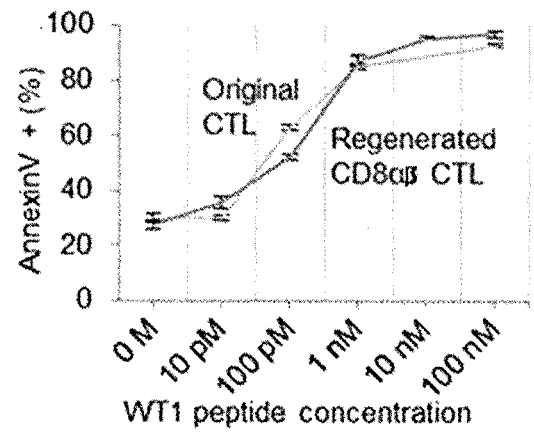
FIG. 16 is a graph showing WT1-peptide specific cytotoxic activities of the CD8SP cells induced from WT1-T-iPS cells according to the procedures shown in FIG. 7 and those the original CTLs from which the WT1-T-iPS cells were established.

The cytotoxic activity of the re-generated CD8SP cells was compared with that of the original WT1 specific CTLs. Results are shown in FIG. 16. The re-generated CD8SP cells exerted WT1 peptide specific cytotoxic activity comparative to that of the original CTLs. In the following Examples 3-5, the re-generated CD8SP cells are referred to as "re-generated CTLs".

Example 3

TCR Specific Cytotoxic Activity of WT1 Specific CD8SP Cells (vs Leukemia Cell Line)

Cytotoxic activities of the regenerated CTLs obtained in Example 2 against WT1-expressing leukemia cells of leukemia cell lines that endogenously express WT1 were evaluated.

Figure 17:
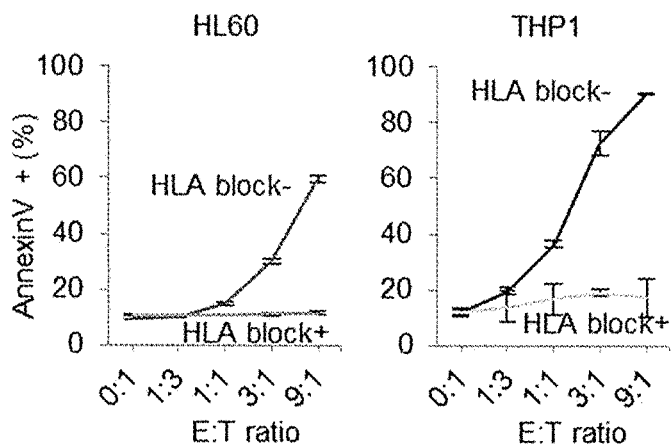
FIG. 17 shows cytotoxic activities of the CD8SP cells induced from WT1-T-iPS cells according to the procedures shown in FIG. 7 against endogenous WT1 protein bearing human leukemia cell line HL60 and THP1. When the target cell's HLA was blocked by an anti-HLA-1 antibody, the cytotoxic activities almost disappeared. Accordingly, the cytotoxic activity of the CD8SP cells was confirmed to be TCR-restricted.

HL60 and THP1 cell lines that endogenously express WT1 protein and derived from HLA A*24:02 positive patients were used to determine in vitro cytotoxic activity of the re-generated CTLs. In order to confirm whether the observed cytotoxic activity is TCR specific, cells from the leukemia cell line were previously incubated in the presence of 10 ng/mL of a HLA-1 inhibiting antibody (clone W6/32) for 1 hour and then, co-incubated with the re-generated CD8SP cells (negative control). The regenerated CTLs and the leukemia cells were mixed so that the ratio is 0:1, 1:3, 3:1 and 9:1 and incubated at 37° C. in a 5% $CO_2$ atmosphere for 6 hours. The cytotoxic activities were determined based on the Annexin V positive cells. Results are shown in FIG. 17.

The cytotoxic activity increased in a cell number dependent manner for any leukemia cell line. On the other hand, the cytotoxic activity was inhibited by HLA-1 inhibiting antibody. Based on the results, the re-generated CTLs induced from WT1-T-iPS cells exert TCR specific cytotoxic activity against the endogenous WT1 antigen.

Example 4

TCR Specific Cytotoxic Activity of WT1 Specific CD8SP Cells (Vs Primary Leukemia Cell Culture)

Figure 18:
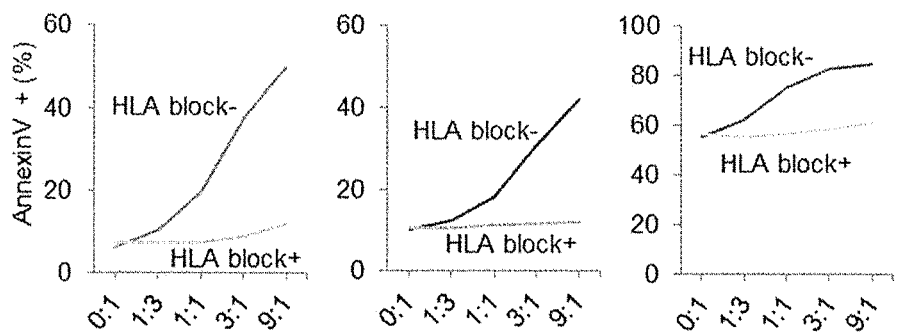
FIG. 18 shows cytotoxic activities of CD8SP cells re-generated from WT1-T-iPS cells according to the procedures shown in FIG. 7 against leukemia cells derived from a patient who is bearing endogenous WT1 protein. The cytotoxic activities against the three types of endogenous WT1 protein bearing-leukemia cells were blocked by anti HLA-1 inhibiting antibody.

Cytotoxic activity of the regenerated CTLs obtained in Example 2 against primary culture of leukemia cells associated with high WT1 expression derived from a HLA A*24:02 positive patient in the same manner as Example 3. In order to confirm whether the observed cytotoxic activity is TCR specific, cells from the leukemia cell line were previously incubated in the presence of 10 ng/mL of a HLA-1 inhibiting antibody (clone W6/32) for 1 hour and then, co-incubated with the re-generated CD8SP cells (negative control). As primary leukemia cells, three types of leukemia cells associated with high WT1 expression were used. The regenerated CTLs and the leukemia cells were mixed so that the ratio is 0:1, 1:3, 3:1 and 9:1 and incubated at 37° C. in a 5% $CO_2$ atmosphere for 6 hours. The cytotoxic activities were determined based on the Annexin V positive cells. Results are shown in FIG. 18.

The cytotoxic activity increased in a cell number dependent manner for any leukemia cells. On the other hand, the cytotoxic activity was inhibited by HLA-1 inhibiting antibody. Based on the results, the re-generated CTLs induced from WT1-T-iPS cells exert TCR specific cytotoxic activity against the primary leukemia cells derived from a patient.

Example 5

Figure 19:
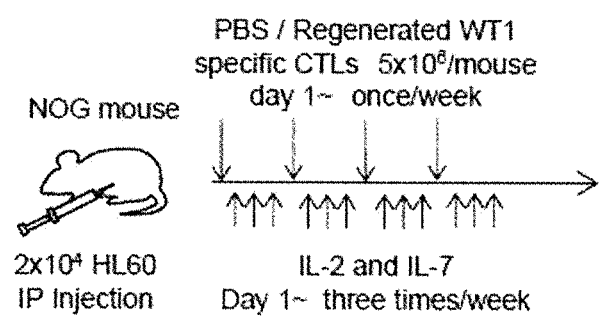
FIG. 19 is an administration schedule of the WT1 specific CD8SP cells (re-generated CTL cells) that were differentiated from WT1-T-iPS cells according to the procedure shown in FIG. 7 to the immuno-deficient mouse inoculated with human acute myeloid leukemia cells in Example 5.

The Function of the Re-Generated CTLs Evaluated In Vivo Using a Mice Heterograft System The outline of the procedures of this example is shown in FIG. 19. Immunodeficient mice NOD.Cg-Prkdcscid Il2rgtm1Sug/Jic (NOG) purchased from Central Institute for Experimental Animals (Kawasaki, Japan) were used. $2 \times 10^4$ cells of WT1 highly expressing, HLA A*24:02-positive and CD3-positive human leukemia cell line HL60 were suspended in PBS and intraperitoneally inoculated to the mice (Day 0). On Day 1, 8, 15 and 22, PBS (control) or the re-generated CD8SP cells (re-generated CTLs) $5 \times 10^6$ cells per administration were intraperitoneally administered to the mice. The experiments were conducted with 5 animals per group. In order to keep the SD8SP cells alive, IL-2 and IL-7 were intraperitoneally administered for 3 times per week for 4 weeks. The peripheral blood was collected on day 37 and day 57 and the presence of the tumor cells or CD33 positive cells as well as the re-generated CTLs or CD8 positive cells in the peripheral blood were confirmed. In addition, the survival time of the mice were confirmed. Results are shown FIGS. 20 and 21.

Figure 20:
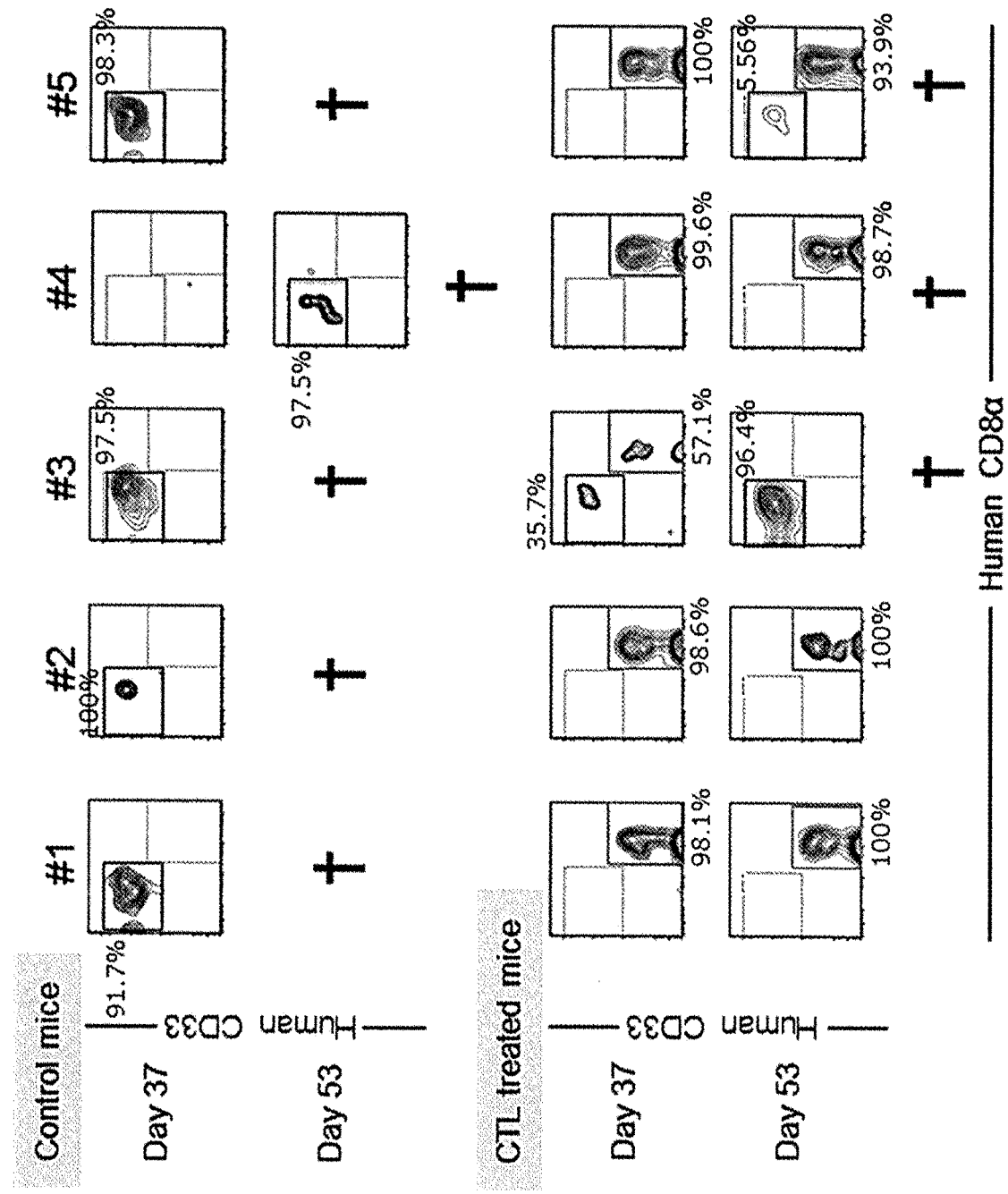
FIG. 20 shows FACS analysis of the peripheral blood obtained from the mouse inoculated with human acute myeloid leukemia cells, after administered with PBS/re-generated CTLs in Example 5.
Figure 21:
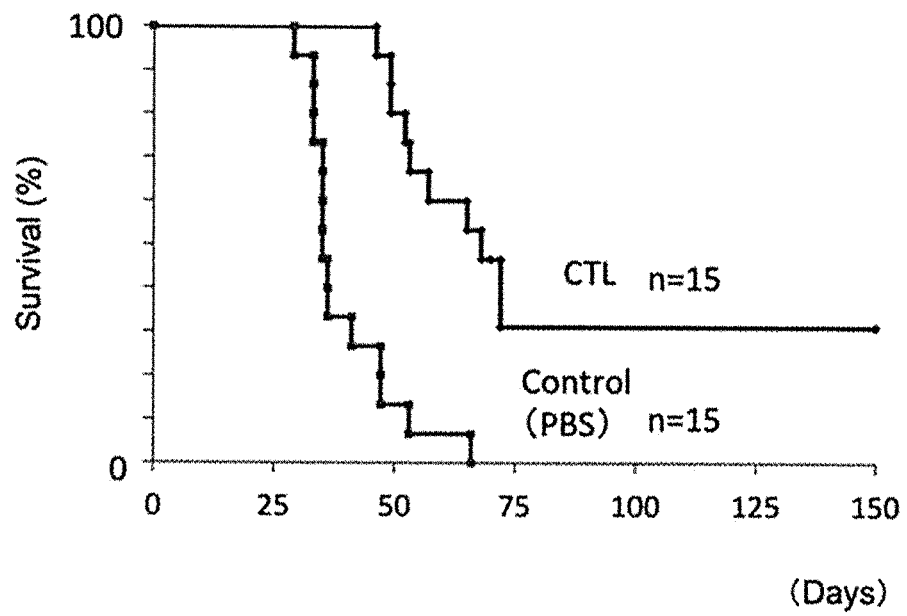
FIG. 21 is a survival curve of the mice inoculated with human acute myeloid leukemia cells and administered with PBS/re-generated CTLs in Example 5. The re-generated CTLs extended the survival period of the mice.

As shown in FIG. 20, tumor cells were observed in the peripheral blood of the control mouse received with PBS while no CD8 T cell was observed in the peripheral blood of the control mouse. On the other hand, transfer of the CD8 T cells in the blood was confirmed in the mice received with the re-generated CTLs while no tumor cell was observed in the peripheral blood. The survival time of the mice received with the re-generated CTLs were significantly longer than the control mice.

After the experiment was completed, all mice were dissected to examine the damage of the tissue. In the mice received with the re-generated CTLs, no tissue damage was observed.

Example 6

Induction of CD8SP Cells from WT1-Peptide Specific TCR-iPS Cells

Establishment of iPS Cells into which WT1 Antigen Specific TCR is Introduced

The original iPS cells used here were iPS cells established from mononuclear cells having a HLA haplotype that is second most frequent in Japanese people in homozygous prepared in Department of Immunology, Institute for Frontier Medicinal Sciences, Kyoto University, Kyoto, Japan.

The iPS cells bearing the WT1 peptide specific TCR genes were prepared by the protocol disclosed in WO2016/010154. The WT1 peptide specific TCR genes, as used herein, were cloned from the regenerated WT1 specific CTLs described in Example 2. Hereinafter, the introduced TCR is referred to as "WT1-TCR".

1) Preparation of WT1-TCR-Containing Lentiviral Vector

CS-UbC-RfA-IRES2-Venus vector was obtained from Subteam for Manipulation of Cell Fate, RIKEN BioResource Center, Tsukuba, Ibaraki, Japan. WT-TCR genes were incorporated in the vector with the Gateway system to give CS-UbC-RfA-IRES2-Venus/WT1-TCR.

2) Obtaining Supernatant of WT1-TCR-Incorporated Lentivirus

CS-UbC-RfA-IRES2-Venus/WT1-TCR was introduced into LentiX-293T packaging cells with X-treamGENE9 (Roche). The medium was exchanged on the next day and on day 2, the culture supernatant was collected and used as lentiviral supernatant.

3) Establishment of WT1-TCR transduced T-iPS cells iPS cells were treated with Tryp LE Select (Life Technologies) to give completely single-cell suspension. The suspension was centrifuged and the pellet was dispersed by the lentiviral supernatant, and then, the obtained suspension was centrifuged at 3000 rpm at 30° C. for one hour so that the iPS cells were infected and the WT1-TCR was introduced into the iPS cells.

After the infection, the cells were suspended in the medium for iPS cells and seeded on the feeder cells. The iPS cells in which WT1-TCR was introduced (WT1-TCR-iPS cells) were fluoroscopically selected on the basis of expression of Venus protein included in the vector. Clones were established independently from the selected cells. One of those clones was selected and subjected to the experiments shown below. Hereinafter, iPS cells obtained by introducing TCR are referred to as "TCR-iPS cells.

Figure 22:
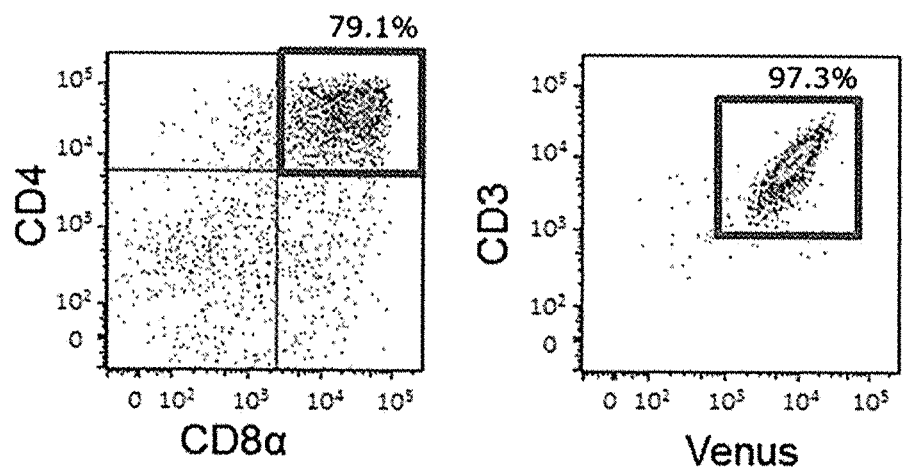
FIG. 22 shows a cell culture on day 40 of the differentiation from TCR-iPS cells into T cells in Example 6.

Thus obtained TCR-iPS cells were differentiated in the same manner as Example 1 (FIG. 7) to give a cell culture comprising DP cells and DN cells (FIG. 22). The cell culture contained 79.1% of DP cells, 12.0% of DN cells and 6.6% of CD8SP cells. DP cells were enriched by using MACS beads. The enriched DP cell culture was induced into CD8 SP cells in the same manner as Example 1 with the exception for using medium D' instead of Medium D.

TABLE 7

Medium D' for differentiating into CD8SP cells

|  | | final conc. |
|---|---|---|
| medium A | 50 mL | |
| hrIL-7 (stock: 10 µg/ml) | 25 µL | 5 ng/mL |
| hrIL-2 (stock: 10000 U/ml) | 50 µL | 100 U/mL |
| CD3Ab (stock: 1 mg/ml) | 3 µL | 60 ng/mL |
| Total | 50.078 mL | |

Figure 23:
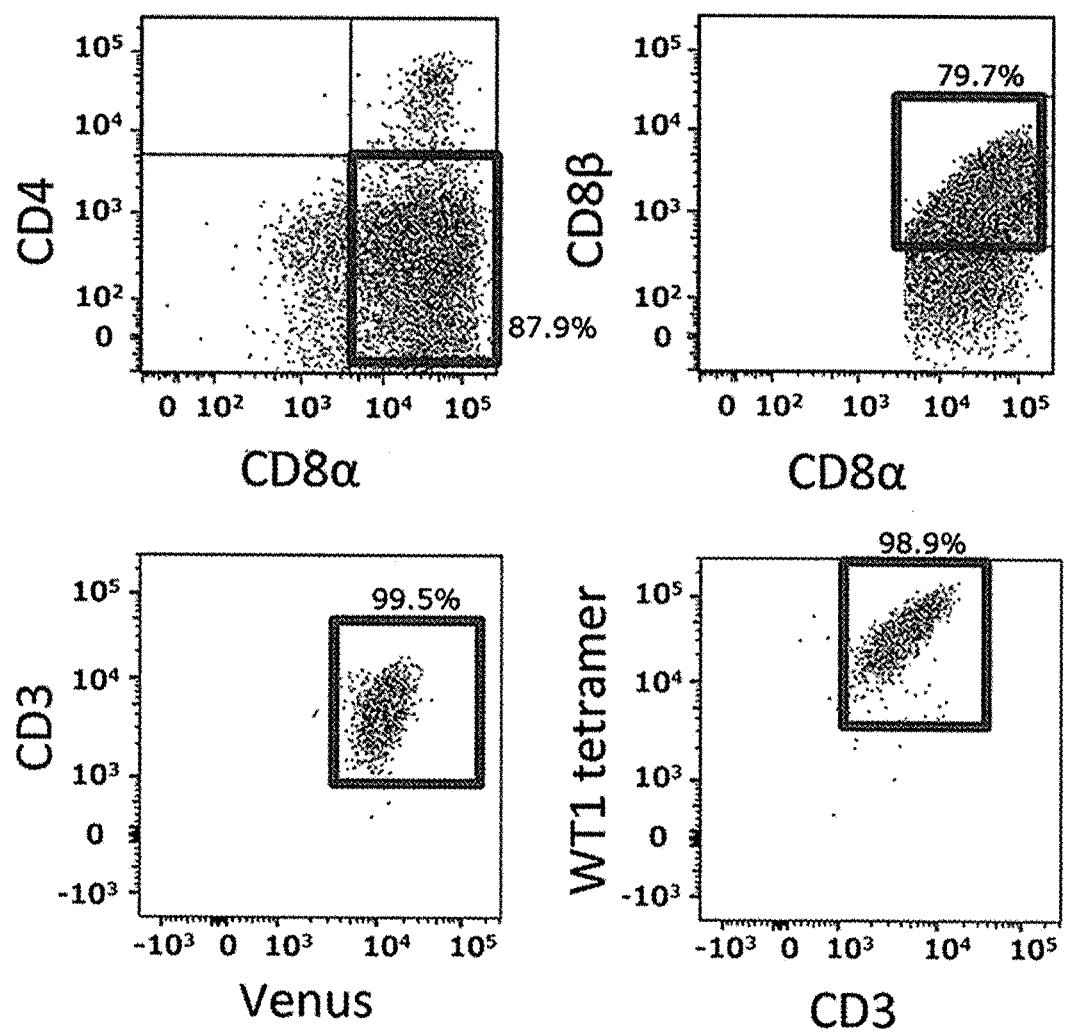
FIG. 23 is a result of FACS analysis of the CD8SP cells induced by stimulating cell culture enriched for DP cells with anti-CD3 antibody. The cell culture in Example 6 was enriched for DP cells on day 40 of the differentiation. Then, the cell culture was stimulated by anti-CD3 antibody. The cells were specific for the WT1 antigen and were CD8$\alpha\beta$ type T cells.

Namely, the enriched DP cell culture was dispersed in medium D' to give a cell suspension at a final concentration of 5×10⁵ cells/mL. Medium in the previously prepared OP9/DLL1 cell culture dish was removed by aspiration, 1 m/well of the cell suspension was seeded on the OP9/DLL1 cell layer and incubated for 6 days. After 6 days incubation, the cells were collected and subjected to the FACS analysis. Results are shown in FIG. 23.

In the cell culture, the percentage of CDSP cells was 87.86%. The CD8SP cells were subjected to FACS analysis and confirmed that 79.7% of the obtained CD8SP cells were CD8αβ type T cells.

Figure 24:
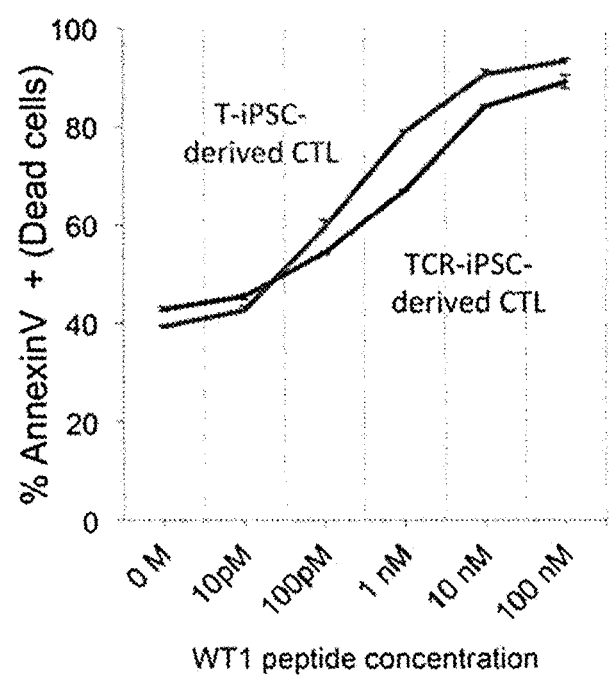
FIG. 24 shows cytotoxic activities of regenerated CTLs induced from TCR-iPS cells obtained in Example 6 and regenerated CTLs induced from T-iPS cells obtained in Example 2. Both of them exerted similar CTL activities.

The cytotoxic activities of the CTLs re-generated from TCR-iPS cells and of those re-generated from T-iPS cells described in Example 2 were compared. Both CTLs expressed the same TCRs. In the manner as shown in FIG. 16, C1R A*24:02 (human LCL cell line) cells were incubated under the presence of various concentration of the WT1 peptide, CYTWNQMNL (SEQ ID No.2) for 2 hours. C1R A*24:02 cells were collected from each culture and mixed with the CD8SP cells to give E:T ratio of 3:1. The cell mixture was incubated for 6 hours at 37° C. in a 5% $CO_2$ atmosphere. After that, cytotoxic activity was determined by the ratio of Annexin V positive cells. Results are shown in FIG. 24. The CTLs re-generated from TCR-iPS cells and those re-generated from T-iPS cells showed similar cytotoxic activities.

What is claimed is:

1. A method for inducing CD4⁻CD8⁺ T cells, comprising the steps of:
   (1) differentiating pluripotent stem cells to give a cell culture comprising CD4⁻CD8⁺ T cells and CD4⁻CD8⁺ T cells,
   (2) differentiating the CD4⁻CD8⁺ T cells in the cell culture obtained in (1) into CD4⁻CD8⁺ T cells under the presence of a substance that inhibits cytotoxic activity of CD4⁻CD8⁺ cells.

2. The method according to claim 1, wherein the substance that inhibits cytotoxic activity of CD4⁻CD8⁺ T cells is selected from the group consisting of a perforin inhibitor, a granzyme inhibitor, a Fas pathway inhibitor, a caspase inhibitor, and an inhibitory antibody against Natural Killer activating receptor.

3. The method according to claim 1, wherein the pluripotent stem cells are iPS cells.

4. The method according to claim 3, wherein the pluripotent stem cells are iPS cells homozygous for HLA haplotype.

5. The method according to claim 1, wherein the pluripotent stem cells comprise rearranged genes encoding a T cell receptor or a chimeric antigen receptor specific for an antigen and CD4⁻CD8⁺ T cells having a cytotoxic activity specific for the antigen are induced.

6. The method according to claim 5, wherein the pluripotent stem cells comprise rearranged genes encoding a T cell receptor specific for the antigen.

7. The method according to claim 6, wherein the pluripotent stem cells are T-iPS cells induced from human T cells comprising rearranged genes encoding a T cell receptor specific for the antigen.

8. The method according to claim 6, wherein the pluripotent stem cells are TCR-iPS cells obtained by introducing rearranged genes encoding a T cell receptor specific for the antigen into human T cells.

9. The method according to claim 5, wherein the step of differentiating CD4⁻CD8⁺ cells into CD4⁻CD8⁺ T cells is performed by directly activating any one of the activation pathways which occur upon stimulation of the T cell receptor.

10. The method according to claim 9, wherein the step of differentiating CD4⁻CD8⁺ cells into CD4⁻CD8⁺ T cells is performed by using anti-CD3 antibody.

11. The method according to claim 9, wherein the step of differentiating CD4⁻CD8⁺ cells into CD4⁻CD8⁺ T cells is performed by stimulating the cells with the antigen.

12. The method according to claim 11, wherein the step of differentiating CD4⁻CD8⁺ cells into CD4⁻CD8⁺ T cells is performed by stimulating the cells with antigen presenting cells that present the antigen.

13. The method according to claim 1, for establishment of CD4⁻CD8⁺ T cells having a cytotoxic activity specific for the antigen, further comprising the step of introducing a T cell receptor or a chimeric antigen receptor specific for the antigen into the induced CD4⁻CD8⁺ T cells.

14. The method according to claim 13, for introducing a T cell receptor specific for the antigen into the induced CD4⁻CD8⁺ T cells.

15. The method according to claim 5, further comprising the step of further proliferating the obtained CD4$^-$CD8$^+$ T cells specific for the antigen.

16. The method according to 15, wherein the step of further proliferating the obtained CD4$^-$CD8$^+$ T cells is performed by directly activating any part of the activation pathway which occurs on stimulating a T cell receptor.

17. The method according to claim 15, wherein the step of further proliferating the obtained CD4$^-$CD8$^+$ T cells is performed by using anti-CD3 antibody.

18. The method according to claim 15, wherein the step of further proliferating the obtained CD4$^-$CD8$^+$ T cells is performed by stimulating the cells with the antigen.

19. The method according to claim 18, wherein the step of further proliferating the obtained CD4$^-$CD8$^+$ T cells is performed by stimulating the cells with antigen presenting cells that present the antigen.

* * * * *

SEQUENCE LISTING

```
<160> NUMBER OF SEQ ID NOS: 2

<210> SEQ ID NO 1
<211> LENGTH: 9
<212> TYPE: PRT
<213> ORGANISM: Homo sapiens

<400> SEQUENCE: 1

Thr Tyr Gly Pro Val Phe Met Ser Leu
1               5

<210> SEQ ID NO 2
<211> LENGTH: 9
<212> TYPE: PRT
<213> ORGANISM: Homo sapiens

<400> SEQUENCE: 2

Cys Tyr Thr Trp Asn Gln Met Asn Leu
1               5
```